US010639269B2

(12) United States Patent
Gerardi et al.

(10) Patent No.: US 10,639,269 B2
(45) Date of Patent: May 5, 2020

(54) COSMETIC COMPOSITIONS COMPRISING TOBACCO SEED-DERIVED COMPONENT

(71) Applicant: R.J. Reynolds Tobacco Company, Winston-Salem, NC (US)

(72) Inventors: Anthony Richard Gerardi, Winston-Salem, NC (US); Barry Smith Fagg, Winston-Salem, NC (US); Thaddeus Jude Jackson, High Point, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 274 days.

(21) Appl. No.: 15/280,459

(22) Filed: Sep. 29, 2016

(65) Prior Publication Data
US 2017/0014332 A1    Jan. 19, 2017

Related U.S. Application Data

(63) Continuation of application No. 13/908,684, filed on Jun. 3, 2013, now abandoned.

(51) Int. Cl.
| | |
|---|---|
| *A61K 36/81* | (2006.01) |
| *A61Q 19/00* | (2006.01) |
| *A61K 8/97* | (2017.01) |
| *A61Q 19/08* | (2006.01) |
| *A61Q 19/10* | (2006.01) |
| *A61Q 5/02* | (2006.01) |
| *A61Q 5/12* | (2006.01) |
| *A61K 8/04* | (2006.01) |
| *A61K 8/92* | (2006.01) |

(52) U.S. Cl.
CPC .............. *A61K 8/922* (2013.01); *A61K 8/04* (2013.01); *A61K 8/97* (2013.01); *A61K 36/81* (2013.01); *A61Q 5/02* (2013.01); *A61Q 5/12* (2013.01); *A61Q 19/00* (2013.01); *A61Q 19/005* (2013.01); *A61Q 19/007* (2013.01); *A61Q 19/08* (2013.01); *A61Q 19/10* (2013.01); *A61K 2800/805* (2013.01)

(58) Field of Classification Search
CPC .......... A61K 36/81; A61K 8/922; A61K 8/97; A61K 8/04; A61Q 19/00; A61Q 19/007; A61Q 19/08; A61Q 19/10; A61Q 5/02; A61Q 5/12
See application file for complete search history.

(56) References Cited

U.S. PATENT DOCUMENTS

| | | |
|---|---|---|
| 2,069,187 A | 1/1937 | Kraybill |
| 2,438,091 A | 3/1948 | Lynch |
| 2,528,378 A | 10/1950 | Mannheimer |
| 2,561,330 A | 7/1951 | Ayers |
| 2,658,072 A | 11/1953 | Kosmin |
| 2,786,858 A | 3/1957 | Vandervoort |
| 2,980,718 A | 4/1961 | Cavanagh et al. |
| 3,069,443 A | 12/1962 | Witte et al. |
| 3,929,678 A | 12/1975 | Laughlin et al. |
| 4,008,210 A | 2/1977 | Steele et al. |
| 4,009,290 A | 2/1977 | Okumori et al. |
| 4,045,879 A | 9/1977 | Witte |
| 4,049,686 A | 9/1977 | Ringers et al. |
| 4,122,104 A | 10/1978 | Witte |
| 4,144,895 A | 3/1979 | Fiore |
| 4,298,540 A | 11/1981 | Youn et al. |
| 4,359,417 A | 11/1982 | Karnofsky et al. |
| 4,456,556 A | 6/1984 | Grimsby |
| 4,456,557 A | 6/1984 | Grimsby |
| 4,466,923 A | 8/1984 | Friedrich |
| 4,506,682 A | 3/1985 | Muller |
| 4,515,726 A | 5/1985 | Sullivan |
| 4,741,855 A | 5/1988 | Grote et al. |
| 4,847,106 A | 7/1989 | Pike et al. |
| 5,077,071 A | 12/1991 | Strop |
| 5,104,646 A | 4/1992 | Bolich, Jr. et al. |
| 5,106,609 A | 4/1992 | Bollich, Jr. et al. |
| 5,248,799 A | 9/1993 | Schmutzler |
| 5,296,621 A | 3/1994 | Roos et al. |
| 5,301,694 A | 4/1994 | Raymond et al. |
| 5,397,571 A | 3/1995 | Roland et al. |
| 5,547,997 A | 8/1996 | Kludas |
| 5,696,278 A | 12/1997 | Segers |
| 5,932,095 A | 8/1999 | Walters et al. |

(Continued)

FOREIGN PATENT DOCUMENTS

| | | |
|---|---|---|
| CN | 103087819 | 5/2013 |
| EP | 0 518 192 | 12/1992 |

(Continued)

OTHER PUBLICATIONS

Bush et al., Sterol Changes during Germination of *Nicotiana tabacum* Seeds, Plant Physiol. (1972) 50, 69-72 (Year: 1972).*

(Continued)

*Primary Examiner* — Michael G. Hartley
*Assistant Examiner* — Nabila G Ebrahim
(74) *Attorney, Agent, or Firm* — Womble Bond Dickinson (US) LLP

(57) ABSTRACT

Cosmetic compositions are provided that include an extract from a seed of the *Nicotiana* species, one or more cosmetically acceptable carriers to act as a diluent, dispersant or carrier for the composition, and optionally one or more cosmetic adjuvants. The tobacco seed extract is typically characterized as having a significant lipid content and, thus, finds use as an oil component in a cosmetic composition.

25 Claims, No Drawings

(56) References Cited

U.S. PATENT DOCUMENTS

| | | |
|---|---|---|
| 5,952,286 A | 9/1999 | Puvvada et al. |
| 6,083,729 A | 7/2000 | Martin et al. |
| 6,106,609 A | 8/2000 | Yang et al. |
| 6,126,950 A | 10/2000 | Bindra et al. |
| 6,139,851 A | 10/2000 | Omura et al. |
| 6,225,483 B1 | 5/2001 | Franke |
| 6,368,639 B1 | 4/2002 | Farooqi et al. |
| 6,403,126 B1 | 6/2002 | Webster et al. |
| 6,414,172 B1 | 7/2002 | Garcés et al. |
| 6,417,157 B1 | 7/2002 | Wadsworth et al. |
| 6,495,175 B2 | 12/2002 | Rao et al. |
| 6,504,085 B1 | 1/2003 | Howard |
| 6,544,530 B1 | 4/2003 | Friedman |
| 6,649,155 B1 | 11/2003 | Dunlop et al. |
| 6,797,172 B2 | 9/2004 | Koseoglu et al. |
| 6,800,318 B2 | 10/2004 | Kapila et al. |
| 6,860,998 B1 | 3/2005 | Wilde |
| 6,861,077 B1 | 3/2005 | Cannell et al. |
| 7,032,601 B2 | 4/2006 | Atchley et al. |
| 7,074,449 B1 | 7/2006 | Holley et al. |
| 7,105,173 B1 | 9/2006 | Rolling |
| 7,156,981 B2 | 1/2007 | Wilde et al. |
| 7,198,808 B2 | 4/2007 | Krasutsky et al. |
| 7,615,657 B2 | 11/2009 | Bathurst et al. |
| 7,741,500 B2 | 6/2010 | Arhancet et al. |
| 8,372,825 B2 | 2/2013 | Turkowitz |
| 8,952,187 B2 | 2/2015 | Kruidenberg |
| 8,956,853 B2 | 2/2015 | Dayton et al. |
| 2002/0121628 A1 | 9/2002 | Kapila et al. |
| 2004/0009242 A1 | 1/2004 | Krasutsky et al. |
| 2005/0042347 A1 | 2/2005 | Bathurst et al. |
| 2005/0147722 A1 | 7/2005 | Fan et al. |
| 2006/0111578 A1 | 5/2006 | Arhancet et al. |
| 2006/0193819 A1 | 8/2006 | Lu et al. |
| 2007/0184123 A1 | 8/2007 | Soulimani |
| 2008/0199418 A1 | 8/2008 | Koroskenyi et al. |
| 2008/0206355 A1 | 8/2008 | Schwartz et al. |
| 2008/0317698 A1 | 12/2008 | Wells et al. |
| 2010/0040758 A1 | 2/2010 | Savngikar et al. |
| 2010/0058655 A1 | 3/2010 | Fogher |
| 2010/0119613 A1 | 5/2010 | Gruber et al. |
| 2010/0135936 A1* | 6/2010 | Dueva-Koganov .... A61K 8/899 424/59 |
| 2010/0203004 A1 | 8/2010 | Simonnet et al. |
| 2010/0239726 A1 | 9/2010 | Pertsovich |
| 2011/0259353 A1 | 10/2011 | Coleman, III et al. |
| 2011/0268675 A1 | 11/2011 | Ureneck et al. |
| 2012/0138074 A1 | 6/2012 | Cantrell et al. |
| 2012/0141648 A1 | 6/2012 | Morton et al. |
| 2012/0192882 A1 | 8/2012 | Dube et al. |
| 2012/0211016 A1 | 8/2012 | Byrd et al. |
| 2012/0238743 A1 | 9/2012 | Kim et al. |
| 2012/0260929 A1 | 10/2012 | Coleman et al. |
| 2012/0272976 A1 | 11/2012 | Byrd et al. |
| 2012/0276210 A1 | 11/2012 | Dihora et al. |
| 2012/0298125 A1 | 11/2012 | Dube et al. |
| 2013/0090279 A1 | 4/2013 | Hilvert et al. |
| 2013/0125904 A1 | 5/2013 | Chen et al. |
| 2013/0276801 A1 | 10/2013 | Byrd, Jr. et al. |
| 2014/0073807 A1 | 3/2014 | Arhancet et al. |
| 2014/0271952 A1 | 9/2014 | Mua et al. |

FOREIGN PATENT DOCUMENTS

| | | |
|---|---|---|
| EP | 1 283 694 | 2/2003 |
| EP | 2 539 032 | 1/2013 |
| JP | 59-28465 | 2/1984 |
| WO | WO 94/288868 | 12/1994 |
| WO | WO 01/89459 | 11/2001 |
| WO | WO 03/063885 | 8/2003 |
| WO | WO 2009/110775 | 9/2009 |
| WO | WO 2010/086724 | 8/2010 |
| WO | WO 2010/093229 | 8/2010 |
| WO | WO-2011046815 A1 * | 4/2011 ............. C10L 1/026 |
| WO | WO 2011/147696 | 12/2011 |

OTHER PUBLICATIONS

Majdi et al., Supercritical Fluid Extraction of Tobacco Seed Oil and its Comparison with Solvent Extraction Methods, J. Agr. Sci. Tech. (2012) vol. 14: 1043-1051 (Year: 2012).*

Ravichandran et al. Evaluation of the efficacy and safety of "Anti-Wrinkle cream" in the treatment of facial skin wrinkles: A prospective, open, phase III clinical trial; The Antiseptic (2005): 102(2), 65-70). (Year: 2005).*

Abbas, M., et al., "Comparative Study on Characteristics of Seed Oils and Nutritional Compostition of Seeds from Different Varieties of Tobacco (*Nicotiana tabacum* L.) Cultivated in Bangladesh," *Asian Journal of Biochemistry*, 2008, pp. 203-212, vol. 3(4).

Bulletin 339, "Chemical Investigations of the Tobacco Plant, III. Tobacco Seed" *Connecticut Agricultural Experiment Station*, 1932.

Carlson et al., "Degumming and Bleaching of *Lesquerella fendleri* Seed Oil," *J. American Oil Chemists' Society*, vol. 70, No. 6, 1993.

Coleman III, W. M., et al., "The use of a non-equilibrated solid phase microextraction method to quantitatively determine the offnotes in mint and other essential oils," *Journal of the Science of Food and Agriculture*, 2004, pp. 1223-1228, vol. 84.

Database GNPD [Online] MINTEL; Feb. 1, 2011 (Feb. 1, 2011), Biologique Recherche: "Crème Dermo-RL," Database accession No. 1496861.

Database GNPD [Online] MINTEL; Jun. 1, 2010 (Jun. 1, 2010), Weleda: "Grenade Firming Night Cream," Database accession No. 1355585.

Database WPI Week 201056 Thomson Scientic, London, GB; AN 2010-K34935 & WO 2010/093229 A1 (LL O M) Aug. 19, 2010 (Aug. 19, 2010)

Desai et al., "Degumming of Vegetable oil by Membrane Technology," *Indian J. Chem. Tech.*, 9:529-534 (2002)

Frega, N., et al., "Chemical Composition of Tobacco Seeds (*Nicotiana tabacum* L.)," *Journal of the American Oil Chemists Society*, 1991, pp. 29-33, vol. 68(1).

Giannelos, P.N., et al., "Tobacco seed oil as an alternative diesel fuel: physical and chemical properties," *Industrial Crops and Products*, 2002, pp. 1-9, vol. 16.

Jude, "Extraction, Characerization and Industrial Applications of Tobacco Seed Oil (*Nicotiana tabacum*)" *Chemisty and Materials Research*, vol. 3(2): pp. 2224-3224 (2013).

List et al., "Supercritical CO2 Degumming and Physical Refining of Soybean Oil," *J. Am Oil Chem Soc.* 70(5): 473-476 (1993)

Majdi, S., et al., "Supercritical Fluid Extraction of Tobacco Seed Oil and its Comparison with Solvent Extraction Methods," *J. Agr. Sci. Tech.*, 2012, pp. 1043.1051, vol. 14.

Moldoveanu et al., "Dual Analysis of Triglycerides from Certain Common Lipids and Seed Extracts," *J. Agric.Food Chem.*, 59, 2137-2147 (2011).

Moldoveanu, "5. Profiling of lipids from fruit and seed extracts", Lipidomics: Sea Food, Marine Based Dietary Supplement, Fruit and Seed, 2012: pp. 73-123, Ed. Su Chen [online], Retrieved from the Internet, [retrieved Oct. 21, 2014], <URL: http://www.trures.com/ebook/uploads/suchencontent/T_13743193085)/020Su%20Chen.pdf>.

Mukhtar, A., et al., "Fatty Acid Composition of Tobacco Seed Oil and Synthesis of Alkyd Resin," *Chinese Journal of Chemistry*, 2007, pp. 705-708, vol. 25.

Patel, J. A., et al., "Production Potential and Quality Aspects of Tobacco Seed Oil," *Tobacco Research*, 1998, pp. 44-49, vol. 24(1).

Ravichandran, G., et al., "Evaluation of the efficacy and safety of "Anti-Wrinkle cream" in the treatment of facial skin wrinkles: A prospective, open, phase III clinical trial,"*The Antiseptic*, 2005, pp. 65-70, vol. 102(2).

Sahraoui, N., et al., "Improved microwave steam distillation apparatus for isolation of essential oils Comparison with conventional steam distillation," *Journal of Chromatography A*, 2008, pp. 229-233, vol. 1210.

(56) References Cited

OTHER PUBLICATIONS

Stanisavijevic et al., "Comparison of Techniques for the Extraction of Tobacco Seed Oil," *Eur. J. Lipid Sci. Technol.*, 2009, 111, pp. 513-518.

Stanisavijevic, I. T., et al., "Ultrasonic Extraction of Oil from Tobacco (*Nicotiana tabacum* L.) seeds," *Ultrasonics Sonochemisny*, 2007, pp. 646-652, vol. 14.

Wiedermann, L. H., "Degumming, refining and bleaching soybean oil," *Journal of the American Oil Chemists Society*, Mar. 1981, pp. 159-166, vol. 58(3).

\* cited by examiner

COSMETIC COMPOSITIONS COMPRISING TOBACCO SEED-DERIVED COMPONENT

CROSS-REFERENCE TO RELATED APPLICATIONS

This application is a continuation application of U.S. application Ser. No. 13/098,684, filed Jun. 3, 2013, which is hereby incorporated by reference in its entirety.

FIELD OF THE INVENTION

The present invention relates to cosmetic products comprising a components made or derived from tobacco. Of particular interest are oil compositions obtained or derived from plant seeds or portions of plant seeds from the *Nicotiana* species.

BACKGROUND OF THE INVENTION

Cosmetics are generally defined as substances used to enhance the appearance or odor of the human body. They are generally mixtures of chemical compounds, some being derived from natural sources and others being synthetic. In the U.S., the Food and Drug Administration (FDA), which regulates cosmetics, defines cosmetics as "intended to be applied to the human body for cleansing, beautifying, promoting attractiveness, or altering the appearance without affecting the body's structure or functions."

There are many different types of cosmetic products, including, but not limited to, hair treatment products such as shampoos and conditioners, body and facial cleansers, skin moisturizing products such as body creams and body lotions, facial products such as eye creams, wrinkle reducing treatments and anti-aging products, make-up products, as well as various other products known in the field. Examples of hair treatment compositions include U.S. Pat. No. 6,139,851 to Omura et al.; U.S. Appl. Pub. Nos. 2013/0090279 to Hilvert et al. and 2012/0276210 to Dihora et al.; and EP 1778181 to Soulimani, each herein incorporated by reference in its entirety. Examples of skin care products include U.S. Pat. No. 6,126,950 to Bindra et al., U.S. Pat. No. 6,544,530 to Friedman et al., U.S. Pat. No. 6,368,639 to Farooqi, U.S. Pat. No. 7,105,173 to Rolling, U.S. Pat. No. 8,372,825 to Turkowitz; U.S. Appl. Pub. No. 2012/0238743 to Kim et al.; EP 1441686 to Dokka et al.; and WO 2010/086724 to Surianarayanan et al., WO 2011/147696 to Chodorowski-Kimmes et al., WO 2003/041636 to Dokka et al., each herein incorporated by reference in its entirety.

Many cosmetic compositions, such as cleansers and shampoo, contain detergents. Sodium lauryl sulfate, ammonium lauryl sulfate, sodium laureth sulfate, ammonium laureth sulfate, stearic acid, lauric acid, myristic acid, oleic acid and palmitic acid are a few of the common detergents or soaps found in cleansers. See, e.g., Antczak, Stephen, and Gina Antczak. *Cosmetics Unmasked: Your Family Guide to Safe Cosmetics and Toiletries*. London: Thorsons, 2001, herein incorporated by reference. Soaps can be made from vegetable oil or animal fats. Coconut oil, olive oil, safflower oil, jojoba oil and tallow, for example, are ingredients used in creating soap-based cleansers. These ingredients are mixed with an alkaline substance, usually sodium hydroxide, or lye, to create a salt. When mixed, in a process called saponification, two byproducts are generally created: glycerin and salt.

Emulsions are among the most common types of delivery systems used in cosmetic formulations. An emulsion is a dispersion of one liquid in a second, immiscible liquid. Typically, cosmetic emulsions include an oily phase comprising one or more hydrophobic, long-chain, organic molecules and an aqueous phase. One or more emulsifiers are typically present to maintain the emulsion in stable form over time.

Various oils can be used in the oily phase of cosmetic compositions in the form of emulsions. Natural oils can be vegetable oils that consist of aethereal salts of glycerin with a large number of organic acids such as stearic acid, oleic acid, and palmitic acid, forming stearin, olein, and palmitin, respectively. Stearin and palmitin are common solid oils and fats used in cosmetic compositions. Olein is a common liquid oil used in cosmetic compositions. Natural oils can function, for example, as excellent emollients that leave the hair and skin soft and smooth. Oils can also penetrate the skin and provide effective nourishing and revitalizing effects. Therefore, natural oils are used in a wide variety of cosmetic products, including personal care as well as makeup products.

A growing number of cosmetic products are directed towards rejuvenating the skin and removing undesirable signs of aging such as wrinkles. Conventional products often contain exfoliating acids as active ingredients. Such anti-aging active ingredients include, for example, a-hydroxy acids (e.g., lactic, glycolic, citric), b-hydroxy acids (e.g., salicylic, 5-n-octanoylsalicylic acids) and retinoids (retinoic acids; retinol). However, these anti-aging acids can be associated with consumer discomfort characterized by burning, stinging, itching or a sensation of tightness after application.

There is a continuing need for new cosmetic compositions that exhibit advantageous properties. Additionally, there remains a general need in the cosmetics industry for products that retard or counter aging effects on the skin without producing undesirable side effects.

SUMMARY OF THE INVENTION

The present invention provides an oil component made or derived from seeds from plants of the *Nicotiana* species useful for incorporation into a variety of cosmetic products. Specifically, a cosmetic composition comprising an extract of a seed of the *Nicotiana* species and at least one cosmetically acceptable carrier, wherein the cosmetic composition is in a form adapted for application to skin or hair is disclosed. In some embodiments, the extract is a tobacco seed oil. In various embodiments, the tobacco seed oil has a free fatty acid content of less than about 15 weight percent, or less than about 10 weight percent, based on the total weight of the tobacco seed oil. In various embodiments of the present invention, the tobacco seed oil comprises at least about 60 weight percent of linoleic acid, based on the total weight of the tobacco seed oil.

In some embodiments, the cosmetic composition is in the form of an emulsion with an aqueous phase and an oily phase comprising tobacco seed oil derived from seeds from plants of the *Nicotiana* species. In various embodiments, the composition is in the form of an emulsion, and comprises a cosmetically acceptable carrier that is an aqueous carrier. In some embodiments of the present invention, the cosmetic composition is in the form of a liquid, a lotion, a gel, a cream, a milk, an ointment, a paste, a plaster, a powder, a foam, a make-up, a stick, an aerosol, or embedded or absorbed in a wipe.

In various embodiments, the cosmetic composition is adapted for use as a body moisturizing oil, a body moisturizing lotion, a body moisturizing gel, a body moisturizing cream, a shaving preparation, a skin powder, a suntan lotion, an anti-acne preparation, a peeling preparation, a shampoo, a hair conditioners, a hair tonic, a hair styling cream, a hair styling gel, a pomade, a hair rinse, a hair-straightening preparation, a hair-setting preparation, a hairspray, a hair dying or bleaching preparation, or a makeup.

In some embodiments of the present invention, the cosmetic composition further comprises one or more cosmetic adjuvants selected from the group consisting of additional fats or lipids, organic solvents, thickeners, binders, conditioning agents, demulcents, opacifiers, stabilizers, buffering agents, humectants, pigments, dyes, viscosity modifiers, emollients, antiperspirants, anti-foaming agents, foam boosters, hair colorants, hair perming agents, hair growth or restorer agents, hair loss prevention agents, abrasives, absorbents, anti-acne agents, anti-caking agents, moisturizing agents, perfumes or fragrances (e.g., bergamot extract), preservatives, sunscreens, astringents, propellants, bleaching or lightening agents for skin or hair, tanning agents, deposition aids, suspending agents, polymers, fillers, sequestrants, bactericides, odor absorbers, antifungal agents, alkalinizing or acidifying agents, pearlescent aids, chelants, proteins, anti-dandruff agents, surfactants, emulsifiers, anti-free radical agents, antioxidants, vitamins, and α-hydroxy acids.

In various embodiments, a cosmetic composition comprising an extract of a seed of the *Nicotiana* species and at least one cosmetically acceptable carrier is provided, wherein the cosmetic composition is in a form adapted for application to skin or hair. The cosmetically acceptable carrier can comprise water and the cosmetic composition can be in the form of a lotion or cream emulsion with an aqueous phase and an oily phase comprising a tobacco seed oil. In addition, the cosmetic composition can further comprise one or more cosmetic adjuvants selected from the group consisting of additional oils, thickeners, surfactants, preservatives, pigments, humectants, emollients, occlusives, and combinations thereof.

In certain embodiments, the cosmetic composition further comprises one or more emollients in an amount of about 0.01 to about 20% by weight of the cosmetic composition. The cosmetic composition can comprise, singly or as mixtures of two or more components, one or more humectants in an amount of about 0.01 to about 10% by weight of the cosmetic composition, one or more surfactants in an amount of about 0.01 to about 50% by weight of the cosmetic composition, one or more conditioning agents in an amount of about 0.01 to about 5% by weight of the cosmetic composition, one or more preservatives in an amount of about 0.01 to about 10% by weight of the cosmetic composition, one or more thickening agents in an amount of about 0.01 to about 15% by weight of the cosmetic composition, one or more emulsifiers in an amount of about 0.01 to about 15% by weight of the cosmetic composition, one or more antioxidants in an amount of about 0.01 to about 10% by weight of the cosmetic composition, one or more natural or essential oils in an amount of about 0.01 to about 20% by weight of the cosmetic composition, one or more occlusives in an amount of about 0.01 to about 5% by weight of the cosmetic composition, and/or one or more agents useful for treating wrinkles in the skin in an amount of about 0.01 to about 5% by weight of the cosmetic composition.

In one embodiment, the cosmetic composition is in the form of an emulsion adapted for moisturizing skin (e.g., a lotion, cream, or body butter), wherein the cosmetic composition comprises water in an amount up to about 80% by weight, a tobacco seed oil in an amount up to about 10% by weight, one or more emollients in an amount up to about 20% by weight, one or more emulsifiers in an amount up to about 15% by weight, and one or more humectants in an amount up to about 10% by weight. In another embodiment, the cosmetic composition is in the form of an emulsion adapted for cleansing skin or hair (e.g., a facial cleanser or shampoo), wherein the cosmetic composition comprises water in an amount up to about 80% by weight, a tobacco seed oil in an amount up to about 10% by weight, one or more emulsifiers in an amount up to about 15% by weight, and one or more surfactants in an amount up to about 50% by weight. Either composition can include one more additional cosmetic adjuvants, such as any of the adjuvants noted herein in any representative amount noted herein.

DETAILED DESCRIPTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

In the present invention, cosmetic compositions are provided that include a tobacco derived component from any portion of a *Nicotiana* plant species. In certain embodiments, cosmetic compositions are provided that include an extract from a seed of the *Nicotiana* species and one or more cosmetically acceptable carriers to act as a diluent, dispersant or carrier for the composition, so as to facilitate its distribution when the composition is applied to the skin or hair. Exemplary carriers include water, and may include, in addition to or in lieu of water, liquid or solid emollients, organic or aqueous co-solvents, humectants, thickeners and powders. Aqueous carriers include water or a miscible mixture of water and an organic co-solvent (e.g., lower alkyl alcohols or polyhydric alcohols). The lower alkyl alcohols useful herein can comprise monohydric alcohols having 1 to 6 carbons. In some embodiments, the solvent comprises ethanol, isopropanol, or a mixture thereof. Polyhydric alcohols useful in cosmetic compositions can include, for example, propylene glycol (PPG-12), hexylene glycol, glycerin, propane diol, and mixtures thereof. In some embodiments, the solvent comprises C13-14 isoparaffin.

The tobacco seed extract may comprise any extracted portion of a seed of the *Nicotiana* species (also referred to generically herein as a tobacco seed extract). Typically, such extracts are characterized as having a significant lipid content and, thus, find use as an oil component in a cosmetic composition. Examples of the types of components that can be present in a tobacco seed extract include various fatty acids and triglycerides. Exemplary fatty acids include palmitic acid, linoleic acid, oleic acid, caprylic acid, myristic acid, pentadecanoic acid, palmetoleic acid, heptadecanoic acid, heptadecenoic acid, elaidic acid, gamma-lenolenic acid, arachidic acid, arachidonic acid, 11-eicosenoic acid, 8,11,14-eicosatrieonic acid, 11, 14,17-eicosatrienoic acid, 5,8,11,14,17-eicosopentanoic acid, heniecosenoic acid, lignoceric acid, 4,7,10,15,19-decosahexanoic acid, and stearic acid. Exemplary triglycerides include trilinolein, palmito-di-linolein, di-palmito-linolein, tripalmitin, tristearin, and triolein.

In certain embodiments, the fatty acid content (including free and triglyceride-bound fatty acids) of the tobacco seed extracts of the invention comprises greater than about 50% by weight linoleic acid, such as greater than about 60% by weight or greater than about 65% by weight. In certain embodiments, the total linoleic acid content is about 65% to about 80% by weight of the fatty acids in the tobacco seed extract. Tobacco seed extracts containing a majority amount of lipids (e.g., greater than about 50% by weight) is referred to herein as tobacco seed oil. Exemplary components of tobacco seed extracts also include a variety of other compounds having flavor and aroma characteristics such as amino acids and various polyphenols.

In many cosmetic products, oil components form an important part of the formulation. Oil components can be categorized into three major groups including oils (including fats/butters), esters, and waxes. All of these groups can function as emollients, but based on their different chemical structures they can also have different additional properties.

Oils and fats differ in that fats are generally solid at room temperature. Both fats and oils are comprised of triglycerides, which are glycerol esters having a glycerol core with attached fatty acids. Fatty acids can be saturated or unsaturated, which can determine the stability and property of the oil. Saturated oils are more stable and do not become rancid as quickly as unsaturated oils. However, unsaturated oils are smoother, less greasy, and in some embodiments, can be absorbed better by the skin.

Linoleic acid is an important fatty acid that the body needs in order to survive. Its benefits are many, encompassing systemic health benefits as well as cosmetic benefits to the skin and hair. Linoleic acid can be derived from animal fats, and also found in vegetable-derived oils, soy lecithin, safflower oil, bitter almond oil, and sunflower oil, for example.

Linoleic acid is an unsaturated fatty acid that can be used, for example, as an emollient and thickening agent in cosmetic compositions. Many of its properties can help skin with problems such as acne, dryness, and swelling. There is some research showing it to be effective in cell regulation and skin-barrier repair, as well as an antioxidant and an anti-inflammatory. *Archives of Dermatological Research*, July 1998, pages 375-381; *Clinical and Experimental Dermatology*, March 1998, pages 56-58; *Journal of Investigative Dermatology*, May 1996, pages 1096-1101; and *Seminars in Dermatology*, June 1992, pages 169-175. In certain embodiments, linoleic acid can enable the skin to hold moisture better such that both a soothing and moisturizing effect is associated with compositions including linoleic acid. For at least these reasons, linoleic acid can be beneficial for many cosmetic products such as lotions, creams, soaps, and even some medications. Accordingly, the high content of linoleic acid found in tobacco seed extracts renders such extracts particularly beneficial in cosmetic formulations.

Addition of the tobacco seed extract of the invention to a cosmetic composition can enhance a cosmetic composition in a variety of ways, depending on the nature of the seed extract and the type of cosmetic composition. Exemplary seed extracts can serve to provide flavor and/or aroma to a cosmetic product (e.g., composition that alters the sensory characteristics of cosmetic compositions). A tobacco seed extract can also provide an advantageous source of linoleic acid in cosmetic products. Tobacco seed oil can replace the oil components conventionally used in cosmetic products.

The high concentration of linoleic acid of the tobacco seed oil can provide beneficial effects on skin and hair, particularly when dealing with problems such as acne, dryness, and swelling. In certain embodiments, cosmetic products incorporating tobacco seed oil can also be effective in cell regulation and skin-barrier repair, as well as provide an antioxidant and an anti-inflammatory effect. Furthermore, tobacco seed oil can be used as an effective and efficient emollient in cosmetic compositions. In some compositions, tobacco seed oil can also function as a surfactant in a cosmetic composition.

Cosmetic compositions of the invention can be in the form of a liquid, a lotion, a thickened lotion, a gel, a cream, a milk, an ointment, a paste, a plaster, a powder, a foam, a make-up, or a stick, and can optionally be packaged as an aerosol such as an aerosol mousse or spray foam, or embedded or absorbed in a wipe. In some embodiments, the compositions according to the invention are provided in the form of a simple or complex emulsion (e.g., O/W, W/O, O/W/O or W/O/W), and more particularly in the form of a lotion or cream.

The tobacco seed extract of the invention can find use in a variety of cosmetic formulations, including skin care preparations (e.g., body oils, body lotions, body gels, treatment creams, skin protection ointments, shaving preparations such as shaving foams or gels, skin powders such as baby powder, moisturizing gels, moisturizing sprays, revitalizing body sprays, cellulite gels, suntan lotions and oils, anti-acne preparations, and peeling preparations); hair care preparations (e.g., shampoos, hair conditioners, hair tonics, styling creams, styling gels, pomades, hair rinses, hair-straightening preparations, hair-setting preparations, hair foams, hairsprays, lacquers, perming agents, and hair dying or bleaching agents); decorative or makeup preparations (e.g., lipstick, eye shadow, mascaras, dry and moist make-up, rouge, and powders); as well as various pharmaceutical formulations applied to skin or hair such as hormone compositions, vitamin compositions, and antimicrobial (e.g., antibacterial or antifungal) compositions.

The compositions of the invention may additionally comprise one or more conventional cosmetic adjuvants, such as additional fat or lipid substances, organic solvents, thickeners, binders, conditioning agents (e.g., hydrocarbon oils, fatty esters, silicones), demulcents, opacifiers, stabilizers, buffering agents, humectants, pigments, dyes, viscosity modifiers, emollients, antiperspirants, anti-foaming agents, foam boosters, hair colorants, hair perming agents, hair growth or restorer agents, hair loss prevention agents, abrasives, absorbents, anti-acne agents, anti-caking agents, moisturizing agents, perfumes or fragrances, preservatives, sunscreens, astringents, propellants, bleaching or lightening agents for skin or hair, tanning agents, deposition aids, suspending agents, polymers, fillers, sequestrants, bactericides and/or odor absorbers, antifungal agents, alkalinizing or acidifying agents, pearlescent aids, chelants, proteins, anti-dandruff agents, surfactants, emulsifiers, anti-free radical agents, antioxidants, vitamins (e.g., vitamins A, B1, B2, B6, B12, C, D, E, etc. and their derivatives), α-hydroxy acids, or any other ingredient normally used in cosmetics. Commonly used natural and synthetic adjuvants are described, for example, in Breslawec, Halyna P., and Tara E. Gottschalck. *International Cosmetic Ingredient Dictionary and Handbook*. Washington, D.C.: Personal Care Products Council, 2012, (hereinafter "Cosmetic Handbook") and Personal Care Products Council (formerly the Cosmetic, Toiletry and Fragrance Association or CTFA) ingredient information (see http://www.personalcarecouncil.org/publicinformation/consumer-ingredient-information), the content of which is hereby incorporated by reference in its entirety.

The amount of tobacco seed extract will vary depending on the type of cosmetic composition and its desired function within the formulation. Typically, tobacco seed extracts can be used in the same amounts conventionally used for lipid components in cosmetic formulations. In certain embodiments, the tobacco seed extract is present in an amount of about 0.1% by weight to about 20% by weight, such as about 1% to about 10% by weight, based on the total weight of the cosmetic formulation. In some embodiments, the amount of tobacco seed extract can be characterized as at least about 0.5% by weight, at least about 1.0% by weight, at least about 1.5% by weight, or at least about 2.0% by weight, based on total weight of the cosmetic formulation.

The cosmetically acceptable carrier will usually form from about 5% to about 99.9%, preferably from about 25% to about 80% by weight of the cosmetic formulation. Typically, the carrier is at least 80% by weight water, based on total weight of the carrier. In certain embodiments, water comprises at least 50% by weight of the inventive composition, most often from about 60 to about 80% by total weight of the composition.

The total amount of various adjuvants contained in the cosmetic formulations of the invention can vary, depending on the cosmetic type and desired functionality of the formulation. In some embodiments, each cosmetic adjuvant will be present in an amount of about 0.1% by weight to about 20% by weight (e.g., about 0.5% to about 10% by weight) and the total adjuvant content will be about 15% to about 40% by weight (e.g., about 20% to about 30% by weight), based on the total weight of the formulation.

Method of Forming Tobacco Seed Extract

The seed material used in the invention is provided from the seed of the plant of the *Nicotiana* species, which is the characteristic reproductive structure of the plant (e.g., seed producing structure). See, for example, Frega et al., *JAOCS*, 68, 29-33 (1991); Patel et al., *Tob. Res.*, 24, 44-49 (1998); Giannelos et al., *Ind. Crops Prod.*, 16, 1-9 (2002); Mukhtar et al., *Chinese J. Chem.*, 25, 705-708 (2007); Stanisavljevic et al., *Eur. J. Lipid Sci. Technol.*, 111, 513-518 (2009); which are incorporated herein by reference.

The selection of the plant from the *Nicotiana* species can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. *Nicotiana* species can be derived using genetic-modification or crossbreeding techniques (e.g., tobacco plants can be genetically engineered or crossbred to increase or decrease production of or to other change certain components, characteristics or attributes). For example, the *Nicotiana* species can be selected on the basis of producing relatively numerous seeds, or producing seeds that incorporate relatively high levels of specific desired components, and the like. Additional information on types of *Nicotiana* species suitable for use in the present invention can be found in US Pat. Appl. Pub. No. 2012/0192880 to Dube et al., which is incorporated by reference herein. Tobacco plants can be grown in greenhouses, growth chambers, or outdoors in fields, or grown hydroponically.

The manner by which the seed is harvested can vary. Typically, the seed is removed from the rest of the plant by cutting or breaking the so-called seed head or seed capsule from the rest of the plant. Virtually all of the seed (e.g., the whole seed) can be harvested and employed as such. Seeds can be isolated using typical mechanical separation and collection techniques.

The time of harvest during the life cycle of the plant can vary. For example, the seed can be harvested when immature, and as such, the inflorescence or flower head can be removed from the plant. Alternatively, the seed head or seed capsule can be harvested from the plant after the point that the seed has reached maturity.

The post-harvest processing of the seed can vary. After harvest, the seed, or portion thereof, can be used in the harvested form (e.g., the seed can be used without being subjected to any curing and/or aging process steps). For example, the seed can be used without being subjected to significant storage, handling or processing conditions. In certain situations, it is preferable that the fresh seed be used virtually immediately after harvest. Alternatively, the tobacco seed material can be subjected to various treatment processes such as, refrigeration, freezing, drying (e.g., freeze-drying or spray-drying), irradiation, yellowing, heating, cooking (e.g., roasting, frying or boiling), fermentation, bleaching or otherwise subjected to storage or treatment for later use. Exemplary processing techniques are described, for example, in US Pat. Appl. Pub. Nos. 2009/0025739 to Brinkley et al. and 2011/0174323 to Coleman, III et al., which are incorporated by reference herein.

At least a portion of the seed of the *Nicotiana* species can be treated with enzymes and/or probiotics before or after harvest, as discussed in U.S. patent application Ser. No. 13/444,272 to Marshall et al., filed on Apr. 11, 2012 and U.S. patent application Ser. No. 13/553,222 to Moldoveanu, filed on Jul. 19, 2012, which are incorporated herein by reference.

The harvested seed can be physically processed. The seed, or parts thereof, can be further subdivided into parts or pieces (e.g., the seed can be comminuted, pulverized, milled or ground into pieces or parts that can be characterized as granules, particulates or fine powders). The seed, or parts thereof, can be subjected to external forces or pressure (e.g., by being pressed or subjected to roll treatment). When carrying out such processing conditions, the seed can have a moisture content that approximates its natural moisture content (e.g., its moisture content immediately upon harvest), a moisture content achieved by adding moisture to the seed or a moisture content that results from the drying of the seed. For example, powdered, pulverized, ground or milled pieces of seed can have moisture contents of less than about 25 weight percent, often less than about 20 weight percent, and frequently less than about 15 weight percent. Parts or pieces of the seed can be used as components of cosmetic products without further processing, or alternatively the particulate seed material can be processed further prior to incorporation into a cosmetic product. The harvested seed, or components thereof, can be subjected to other types of processing conditions. For example, components of the seed can be separated from one another, or otherwise fractionated into chemical classes or mixtures of individual compounds, as set forth more fully below, in order to form a tobacco seed extract.

Typical separation processes can include one or more process steps such as solvent extraction (e.g., using polar solvents, non-polar organic solvents, or supercritical fluids), chromatography, distillation, filtration, cold pressing or other pressure-based techniques, recrystallization, and/or solvent-solvent partitioning. Exemplary extraction and separation solvents or carriers include water, alcohols (e.g., methanol or ethanol), hydrocarbons (e.g., heptane and hexane), diethyl ether methylene chloride and supercritical carbon dioxide. Exemplary techniques useful for extracting components from *Nicotiana* species are described in or referenced in US Pat. Appl. Pub. Nos. 2011/0259353 to Coleman, III et al. and 2012/0211016 to Byrd, Jr. et al., which are incorporated by reference herein. Various other additives can be used in the extraction process, including, but not limited to, surfactants and co-solvents.

The conditions of the extraction process can vary. In some embodiments, the seed of the *Nicotiana* species is combined with a solvent to form a suspension or slurry. In certain embodiments, the amount of solvent added can be at least about 50 weight percent, or at least about 60 weight percent, or at least about 70 weight percent, based on the total weight of the suspension or slurry. In some cases, the amount of solvent can be described as at least about 80 weight percent or at least about 90 weight percent.

The temperature and pressure of the extraction process can vary. Exemplary temperatures include room temperature or an elevated temperature, such as greater than about 50° C., greater than about 60° C., greater than about 70° C., greater than about 80° C., or greater than about 90° C. Typical pressures experienced during extraction range from about atmospheric pressure to about 1,000 psig.

The amount of time required to effectuate extraction is partially dependent on the temperature and pressure at which the extraction is conducted. For example, in some embodiments, heating the material to an elevated temperature and/or pressurizing the material increases the rate of extraction. The time range for the extraction process is typically at least about 30 minutes (e.g., at least about 1 hour or at least about 2 hours) and typically less than about 24 hours (e.g., less than about 12 hours or less than about 8 hours), although other time periods could be used without departing from the invention. In some embodiments, multiple extractions can be conducted to extract additional compounds therefrom. See, for example, US Patent App. Publ. No. 2008/0254149 to Havkin-Frenkel, which is incorporated herein by reference.

In some embodiments, a tobacco extract described herein is further treated by filtration. Extracts can, in some embodiments, comprise some level of solid (insoluble) material entrained in the liquid. Following extraction, an extracted liquid component can thus be filtered to remove at least some of the solids. In other words, some or all of the portion of the plant material that is insoluble in the extraction solvent is removed. The process of filtration can comprise passing the liquid through one or more filter screens to remove selected sizes of particulate matter. Screens may be, for example, stationary, vibrating, rotary, or any combination thereof. Filters may be, for example, press filters or pressure filters. In some embodiments, the filtration method used can involve microfiltration, ultrafiltration, and/or nanofiltration. A filter aid can be employed to provide effective filtration and can comprise any material typically used for this purpose. For example, some common filter aids include cellulose fibers, perlite, bentonite, diatomaceous earth, and other siliceous materials. To remove solid components, alternative methods can also be used, for example, centrifugation or settling/sedimentation of the components and siphoning off of the liquid.

Although in some embodiments, the tobacco extract is used directly, it may be desirable to thermally treat the tobacco extract in order to, for example, pasteurize the material or otherwise chemically alter the material. This thermal treatment can be conducted before or after any of the processes described herein for the extraction of one or more components from a plant of the *Nicotiana* species. For example, a tobacco extract can be thermally processed by mixing the tobacco extract, water, and an additive such as an amino acid or asparaginase; and heating the moist tobacco mixture at a temperature of at least about 60° C. to form a heat-treated tobacco mixture. Such heat treatment can help prevent acrylamide production resulting from reaction of asparagine with reducing sugars in tobacco materials and can provide some degree of pasteurization. See, for example, US Pat. Pub. No. 2010/0300463 to Chen et al., which is incorporated herein by reference.

Additionally, the tobacco extract can be brought into contact with an imprinted polymer or non-imprinted polymer such as described, for example, in US Pat. Pub. Nos. 2007/0186940 to Bhattacharyya et al; 2011/0041859 to Rees et al.; and 2011/0159160 to Jonsson et al; and U.S. patent application Ser. No. 13/111,330 to Byrd et al., filed May 19, 2011, all of which are incorporated herein by reference. Treatment with a molecularly imprinted or non-imprinted polymer can be used to remove certain components of the extract, such as Hoffmann analytes.

Various methods of solvent removal can be employed, such as heat treatment to evaporate the solvent, reverse osmosis membrane treatment, spray drying or freeze drying. In one embodiment, the concentration process can entail heating the extracted liquid in a vented vessel to evaporate a portion of the water. The temperature and pressure at which the liquid is heated may vary. See, for example, the solvent removal techniques set forth in US Pat. Pub. No. 2012/0152265 to Dube et al., which is incorporated by reference herein.

Of particular interest in the present invention is the oil that can be extracted from the tobacco seeds. Methods of extracting oil components from plant seeds are described, for example, in U.S. Pat. No. 4,008,210 to Steele et al.; U.S. Pat. No. 4,009,290 to Okumori et al.; U.S. Pat. No. 4,045,879 to Witte; U.S. Pat. No. 4,122,104 to Witte; U.S. Pat. No. 4,298,540 to Youn et al.; U.S. Pat. No. 4,359,417 to Karnofsky et al.; U.S. Pat. No. 4,456,556 to Grimsby; U.S. Pat. No. 4,456,557 to Grimsby; U.S. Pat. No. 4,466,923 to Friedrich; U.S. Pat. No. 4,515,726 to Sullivan; U.S. Pat. No. 4,847,106 to Pike et al.; U.S. Pat. No. 5,077,071 to Strop; U.S. Pat. No. 5,296,621 to Roos et al.; U.S. Pat. No. 5,397,571 to Roland et al.; U.S. Pat. No. 5,932,095 to Walters et al.; U.S. Pat. No. 6,083,729 to Martin et al.; U.S. Pat. No. 6,225,483 to Franke; U.S. Pat. No. 6,403,126 to Webster et al.; U.S. Pat. No. 6,414,172 to Garces et al.; U.S. Pat. No. 6,417,157 to Wadsworth et al.; U.S. Pat. No. 6,495,175 to Rao et al.; U.S. Pat. No. 6,504,085 to Howard; U.S. Pat. No. 6,860,998 to Wilde; U.S. Pat. No. 7,074,449 to Holley et al.; and U.S. Pat. No. 7,156,981 to Wilde et al.; US Patent Appl. Pub. Nos. 2002/0121628 to Kapila et al.; 2004/0009242 to Krasutsky et al.; 2005/0042347 to Bathurst et al.; 2005/0147722 to Fan et al.; 2006/0111578 to Arhancet et al., and 2011/0259353 to Coleman III et al.; and WO 2009/110775 to Murzagaliyev et al., all of which are incorporated by reference herein.

There are a number of methods for extracting tobacco seed oil. The relevant part of the plant may be placed under pressure to extract the oil, which provides an expressed oil. Oils may also be extracted from tobacco by dissolving tobacco seeds in a suitable solvent. The solution is then separated from the plant material and concentrated, giving an extracted or leached oil. Alternatively, the oil can be extracted by distilling the oil away from the plant material, thereby giving an essential oil. A fourth method includes infusing parts of plants in a base oil, a process called liquid-liquid extraction, and thereby making a macerated oil.

Components of the tobacco seed can be subjected to conditions so as to cause those components (whether as part of the seed or in the form of a seed extract) to undergo chemical transformation. For example, seed extracts that have been separated from the seed can be treated to cause chemical transformation. The chemical transformations or modification of the seed extract can result in changes of certain chemical and physical properties of those seed extracts (e.g., the sensory attributes of those extracts). Exemplary chemical modification processes can be carried out by acid/base reaction, hydrolysis, heating (e.g., a thermal treatment where the seed isolate is subjected to an elevated temperature such as a temperature of at least about 50° C. or at least about 75° C. or at least about 90° C.), and enzymatic treatments (e.g., using hydrolyase, glycosidase, or glucocidase); and as such, components of the seed extract can undergo esterification, transesterification, isomeric conversion, acetal formation, acetal decomposition, and the like. Additionally, various isolated lipid components of the seed extract can be subjected to hydrogenation in order to alter the degree of saturation of those components, and hence alter the physical form or behavior of those components.

In one aspect, tobacco seed can be cold pressed in order to squeeze lipids from the seed, and those lipid components are collected and optionally further isolated; or alternatively the seed can be subjected to solvent extraction using a solvent (e.g., a polar solvent or a non-polar organic solvent), and the resulting extract is collected and the extracted components are optionally further isolated. Still further, tobacco seed material is optionally subjected to enzymatic treatment to form an enzymatically-treated seed material. The enzymatically-treated material then is subjected to solvent extraction to form a seed extract.

In one embodiment, the separating or isolating process comprises freezing a harvested seed or a portion thereof to form a frozen seed material, processing the frozen seed into a particulate form, subjecting the particulate seed material to an enzymatic treatment to chemically alter the particulate seed material, and extracting the particulate seed material with a solvent to produce a seed extract. Exemplary enzymatic treatments include treatment with a glycosidase or a glucocidase.

Refining tobacco seed oil can provide advantageous compositions useful in the present invention. For example, in various embodiments, raw oil comprises about 80% by weight triglyceride bound fatty acids and about 20% free fatty acids. In contrast, refined oil can comprise about 96-99% triglyceride bound fatty acids and only about 1-4% free fatty acids. Regardless of whether the fatty acids are free or bound, the proportion of fatty acids in various embodiments of tobacco seed oil can be about 69-71% by weight linoleic acid, about 11-13% oleic acid, about 8-11% palmitic, about 3-5% stearic acid, and about 2-3% various other medium chained fatty acids. Tobacco seed oil can be characterized by analysis of free fatty acids by using trimethylsilylation (TMS) derivatization followed by GC-MS analysis. For triglyceride bound fatty acids, the fatty acids are base hydrolyzed from glycerin and then analyzed by the same method. Fatty acid content can also be measured by using standardized methods provided by the Association of Analytical Communities (AOAC) or the American Oil Chemists Society (AOCS).

A tobacco seed oil of the invention can be further refined in order to reduce the free fatty acid content thereof in order to enhance storage stability. For example, in certain embodiments, a crude tobacco seed oil will have about 20% to about 30% by weight free fatty acid content. Both physical and chemical refining techniques (or combinations thereof) can be used. Physical techniques include distillation, which separates the free fatty acids from the desired triglycerides based on difference in boiling point. A typical chemical refining technique involves alkaline neutralization of the fatty acids, dilution of the resulting aqueous-soluble phase, and separation of the neutralized acids from the remaining lipid components, such as by centrifugation. In certain embodiments, the refined tobacco seed oil of the invention has a free fatty acid content of less than about 15% by weight, such as less than about 10% by weight, less than about 8% by weight, or less than about 5% by weight, based on the total weight of the tobacco seed oil.

The form of the tobacco seed extract can vary. Typically, the seed extract is in a solid, liquid, or semi-solid or gel form. The seed extract can be used in concrete, absolute, or neat form. The seed extract can have a dry particulate form, a waxy form, or a thick paste form. The tobacco extract can also be used in an encapsulated form, such as encapsulated within microcapsules having an outer wall and an inner payload that includes the extract.

Although particularly advantageous embodiments of the invention focus on extracts from tobacco seeds, such as tobacco seed oil, other components of the tobacco plant or extracts thereof could also be used in a cosmetic formulation. For example, components of a tobacco plant, such as leaves, stem, stalk, roots, lamina, flowers, and various portions and combinations thereof (or extracts therefrom), could be used in a cosmetic formulation. Extracts from such tobacco plant components can include, for example, terpenes, sesqui-terpenes, diterpenes, esters (e.g., terpenoid esters and fatty acid esters), alcohols, aldehydes, ketones, carboxylic acids, lactones, anhydrides, phenols quinones, ethers, nitriles, amines, amides, imides, nitroalkanes, nitrophenols, nitroarenes, nitrogen-containing heterocyclics, lactams, oxazoles, aza-arenes, sulfur-containing compounds, alkaloids (e.g., nicotine), plastid pigments (e.g., chlorophylls or carotenoids), lipids (e.g., phytosterols), and derivatives thereof. Extracts from various portions of the tobacco plant can serve various functions within a cosmetic, such as enhancement of sensory characteristics (e.g., by providing an aroma or flavor), serving as a binder or filler, or otherwise augmenting or replacing conventional cosmetic ingredients. Various references in the art teach methods of extracting or deriving components from tobacco, such as starch or sugar (U.S. Appl. Pub. Nos. 2012/0138074 to Cantrell et al. and 2012/0141648 to Morton et al.), polymeric or bioplastic materials (U.S. Appl. Pub. Nos. 2012/0192882 to Dube et al. and 2012/0211016 to Byrd et al.), glycerin (U.S. Appl. Pub. No. 2012/0260929 to Coleman et al.), various flavorful or aromatic compounds (U.S. Appl. Pub. No. 2012/0272976 to Byrd et al.), triacetin (U.S. Appl. Pub. No. 2012/0298125 to Dube et al.), pectin (U.S. Appl. Pub. No. 2013/0125904 to Chen et al.), microcrystalline cellulose (U.S. application Ser. No. 13/451,032 to Byrd et al.), and proteins (U.S. application Ser. No. 13/830,063 to Mua et al.), all of which are incorporated by reference herein.

Exemplary Cosmetic Adjuvants

In addition to tobacco seed extract (e.g., tobacco seed oil), cosmetic compositions of the invention can comprise various other ingredients depending on the desired purpose of the composition. It should be understood that although the following exemplary adjuvants may be identified as a certain type/class of adjuvant, or for a particular purpose/function within the cosmetic composition, various ingredients have several purposes that may not be listed herein. Therefore, an adjuvant can serve multiple functions in a composition, despite the non-limiting classifications and examples below.

Certain compositions of the present invention can comprise an emulsifier, particularly where the cosmetic uses the tobacco seed oil as at least a portion of the oily phase of an emulsion. Emulsifiers, which can be synthetic or natural, can be useful to blend ingredients that otherwise would be immiscible. Natural emulsifiers can include, for example, olive oil, olive oil/wheat protein, olive oil/oat protein, sucrose esters, rice bran emulsifiers, and or various other food and pharmaceutical grade emulsifiers, alone or in combination. Synthetic emulsifiers can include, for example, silicone emulsifiers, such as dimethicone copolyols; sulfonates and sulfonic acids derivatives; phosphorous organic derivatives; sugar esters; fatty esters, such as sorbitan monolaurate, sorbitan stearate, sorbitan laurate, sorbitan palmitate, sorbitan oleate, cetearyl olivate, sorbitan olivate; polyesters/PEG (polyethylene glycol) derivatives, such as Polysorbate 20 (polyethylene glycol 20 sorbitan monolaurate); fatty acid esters of fatty alcohols, such as glyceryl stearate, isopropyl stearate, hexyl laurate; fatty acid amides; acyl lactylates; alkoxylated compounds, such as alkoxylated block polymers, alcohols, alkylphenols, amines, amides, fatty esters, fatty acids, oils, sugar esters and polyesters, fatty acid esters of fatty alcohols, and ethers of fatty alcohols; carboxylated alcohol ethoxylates and alkylphenol ethoxylates; carboxylic acids/fatty acids; bases such as triethanolamine; fatty alcohols such as cetearyl alcohol, and mixtures thereof. The total amount of an emulsifier contained in the cosmetic formulations of the invention can vary. In some embodiments, an emulsifier will be present in an amount of about 0.01% by weight to about 20% by weight, or about 0.1% to about 10% by weight, or about 0.5% to about 5% by weight, based on the total weight of the formulation.

Compositions according to the present invention also can include one or more essential and natural oils. In certain embodiments, the one or more oils is present in an amount of about 0.1% by weight to about 20% by weight, such as about 1% to about 10% by weight, based on the total weight of the cosmetic formulation. In some embodiments, the amount of oils can be characterized as at least about 0.5% by weight, at least about 1.0% by weight, at least about 1.5% by weight, at least about 2.0% by weight, or at least about 5% by weight, based on total weight of the cosmetic formulation. As described above, tobacco seed oil can be substituted for oils traditionally used in cosmetic compositions; however, other essential and natural oils can be used in addition to tobacco seed oil in some embodiments. Natural oils can include, for example, jojoba oil, sweet almond oil, coconut oil, shea butter, mango butter, and/or aloe vera butter or mixtures thereof. Essential oils can be synthetic or natural. Natural essential oils can include, for example, bergamot, chamomile german, chamomile maroc, chamomile roman, cinnamon zeylanicum, clove buds, *eucalyptus globulus*, frankincense, fennel, hyssop, juniper, lemon grass, mountain savory, niaouli, peppermint, red thyme, rosemary, rose geranium, tagestes, and ylang ylang.

Synthetic essential oils can include, for example, esters, such as acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, PEG-4 diheptanoate, hydrogenated castor oil, isotridecyl isononanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, tridecyl octanoate, octyl palmitate, dioctyl malate, tridecyl octanoate, myristyl myristate, octododecanol; fatty alcohols such as oleyl alcohol, isocetyl alcohol; and also silicone oils, isoparaffins, hydrogenated polyisobutene, petrolatum, lanolin derivatives, and sorbitan derivatives. Other natural and synthetic oils can be found in the Cosmetic Handbook and Personal Care Products Council ingredient information.

Embodiments of compositions according to the present invention also can include thickeners, which can be used to gel or thicken cosmetic compositions. In certain embodiments, thickeners can provide, for example, better deposition properties of the cosmetic product. When present in the cosmetic composition, the thickening agent can be included in an amount from about 0.01% to about 10%, alternatively from about 0.1% to about 5%, by weight of the composition. Thickeners can be either synthetic or natural. Natural thickeners can include waxes, gums and powders and mixtures thereof. Natural waxes can include, for example, beeswax, carnauba, and/or candelilla and mixtures thereof. Natural gums can include, for example, acacia, xanthan, schelortium (amigel), and/or cellulose and mixtures thereof. Natural powders can include, for example, clay, diatomaceous earth, fuller's earth, silica, silica shells or spherical silica, fumed silica, spherical silica, hydrated silica, silica silylate, mica, titanated mica, talc, cellulose or spherical cellulose beads, microcrystalline cellulose, corn starch, rice starch, glyceryl starch, soy flour, walnut shell powder, agar, sericite, dextran, nylon, silk powder, chalk, calcium carbonate, bismuth oxychloride, iron oxide, titanium dioxide, aluminum silicate, magnesium aluminum silicate, calcium silicate, magnesium trisilicate, aluminum starch octenylsuccinate, bentonite, hectorite, kaolin, maltodextrin, montmorillonite, zinc laurate, zinc myristate, zinc rosinate, alumina, attapulgite, tin oxide, titanium hydroxide, trimagnesium phosphate, or mixtures thereof.

Synthetic thickeners can include, for example, AMP isostearoyl hydrolyzed collagen, AMP isostearoyl hydrolyzed wheat protein, ammonium acryloyldimethyltaurate VP copolymer, cetyl hydroxyethylcellulose, chondroitin sulfate, cocoamidopropyldimethylamine $C_{8-16}$ isoalkysuccinyl lactoglobulin sulfonate, cocodimonium hydroxypropyl hydrolyzed collagen, distarch phosphate, ethyl ester of hydrolyzed animal protein, guar hydroxypropyltrimonium chloride, glyceryl polymethacrylate, hydrolyzed animal or plant protein, hydroxypropyl guar, hydroxypropylmethyl cellulose, hydroxypropyl cellulose, isostearoyl hydrolyzed collagen, methylcellulose, nitrocellulose, nonoxynyl hydroxyethylcellulose, acrylate polymers, acrylamine polymers, acrylic acid polymers (carbomer), PVMIMA Decadiene crosspolymers, polyvinylpyrrolidone polymers, silicone oils, polyethylene thickeners, aluminum starch octenyl succinate, trihydroxystearin, and mixtures thereof. Other natural and synthetic thickeners can be found in the Cosmetic Handbook and Personal Care Products Council ingredient information.

As noted above, compositions according to the present invention can include waxes. In some embodiments, suitable waxes can have a melting point ranging from 35 to 120° C., and include, for example, natural and synthetic waxes. When present in the cosmetic composition, a wax can be included in an amount from about 0.01% to about 10%, alternatively from about 0.1% to about 5%, by weight of the composition. Natural waxes can be, for example, esters of fatty acids and a long chain alcohol. Natural waxes can include, for example, bayberry wax, beeswax, candelilla wax, carnauba wax, hydrogenated jojoba oil, hydrogenated jojoba wax, hydrogenated microcrystalline wax, hydrogenated rice bran wax, Japan wax, jojoba butter, jojoba oil, jojoba wax, mink, ouricury, ozokerite, rice bran, and/or shellac. In an embodiment, the cosmetic composition comprises beeswax, which functions as a useful emollient and thickener. Synthetic waxes can include, for example, ceresin, cetyl esters (e.g., cetyl palmitate or cetyl ester wax, both of which can replace spermaceti, a natural wax originally obtained from whales), lanolin wax, microcrystalline wax, montan, montan acid wax, paraffin, PEG-6 beeswax, PEG-8 beeswax, polyolefin, sulfurized jojoba oil, synthetic beeswax (i.e., hydroxyoctacosanyl hydroxystearate), synthetic candelilla wax, synthetic carnauba wax, synthetic Japan wax, synthetic jojoba oil, synthetic wax, stearoxy dimethicone, dimethicone behenate, stearyl dimethicone, and synthetic homo- and copolymer waxes from the ethylene series or mixtures thereof, waxes obtained by Fischer-Tropsch synthesis, waxy copolymers and esters thereof, and silicone waxes. In some embodiments, emulsifying waxes, a special group of synthetic waxes, can be incorporated into a cosmetic composition to serve primarily as an emulsifier as opposed to an emollient. Other natural and synthetic waxes can be found in the Cosmetic Handbook and Personal Care Products Council ingredient information.

Embodiments of cosmetic compositions according to the present invention can comprise a surfactant, also referred to as a detersive component or soap. The surfactant can provide cleaning performance to the composition. In various embodiments, surfactants can be used to enhance lather volume of a cosmetic composition. In some embodiments, surfactants can provide texture to the cosmetic product. The surfactant can comprise an anionic surfactant, zwitterionic or amphoteric surfactant, or combinations thereof. Various examples and descriptions of detersive surfactants are set forth in U.S. Pat. Nos. 5,104,646, 6,106,609, and 6,649,155; U.S. application Ser. No. 12/103,902; and U.S. Appl. Pub. No. 2008/0206355, and are incorporated herein by reference in their entireties. Other surfactants can be found in the Cosmetic Handbook and Personal Care Products Council ingredient information. When present in the cosmetic composition, one or more surfactants can be included in an amount from about 2% to about 50%, from about 5% to about 30%, from about 10% to about 25%, or from about 1% to about 10%, by weight of the composition.

Non-limiting examples of suitable anionic surfactants include alkyl and alkyl ether sulfates of the formula $ROSO_3M$ and $RO(C_2H_4O)_xSO_3M$, wherein R is alkyl or alkenyl of from about 8 to about 18 carbon atoms, x is 1 to 10, and M is a water-soluble cation such as ammonium, sodium, potassium, and triethanolamine cation or salts of the divalent magnesium ion with two anionic surfactant anions. The alkyl ether sulfates can be made as condensation products of ethylene oxide and monohydric alcohols having from about 8 to about 24 carbon atoms. The alcohols can be derived from fats such as coconut oil, palm oil, palm kernel oil, or tallow, or can be synthetic. These ingredients can be mixed with an alkaline substance, usually sodium hydroxide, or lye, to create a salt. Other suitable anionic surfactants include water-soluble salts of the organic, sulfonic acids of the general formula $[R^1—SO_3M]$, wherein $R^1$ is a straight chain aliphatic hydrocarbon radical having from 13 to 17 carbon atoms, and M is a water soluble cation such as ammonium, sodium, potassium, and triethanolamine cation or salts of the divalent magnesium ion with two anionic surfactant anions.

Anionic surfactants suitable for use herein include, for example, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, sodium C14-16 olefin sulfonate, and mixtures thereof.

In various embodiments, amphoteric surfactants suitable for use in cosmetic compositions can be broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. In some embodiments, for example, amphoteric surfactants for use in the cosmetic composition comprise sodium 3-dodecyl-aminopropionate, sodium 3-dodecylaminopropane sulfonate, sodium lauryl sarcosinate, N-alkyltaurines, N-higher alkyl aspartic acids, cocoamphoacetate, cocoamphodiacetate, lauroamphoacetate, lauroamphodiacetate, and mixtures thereof.

In some embodiments, zwitterionic surfactants suitable for use in a cosmetic composition can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In some embodiments, for example, zwitterionic surfactants for use in the cosmetic composition comprise betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxy ethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines can include coco dimethyl sulfopropyl betaine, stearyl dimethyl sulfopropyl betaine, lauryl dimethyl sulfoethyl betaine, lauryl bis-(2-hydroxyethyl) sulfopropyl betaine, and mixtures thereof.

In certain embodiments, cationic and nonionic surfactants can be used in cosmetic compositions. Cationic surfactants can be derived from amines that are protonated at the pH of the formulation, e.g. bis-hydroxyethyl lauryl amine, lauryl dimethylamine, lauroyl dimethyl amidoproplyl amine, cocoylamidopropyl amine, and the like. Cationic surfactants can also be derived from fatty quaternary ammonium salts such as lauryl trimethylammonium chloride and lauroylamidopropyl trimethyl ammonium chloride.

Nonionic surfactants can comprise water soluble components such as lauryl dimethylamine oxide, cocodimethylamine oxide, cocoamidopropylamine oxide, laurylamidopropyl amine oxide, etc., or alkylpolyethoxylates such as laureth-4 to laureth-7. Nonionic surfactants can also comprise and water insoluble components such as cocomonoethanol amide, cocodiethanol amide, lauroylmonoethanol amide, alkanoyl isopropanol amides, and fatty alcohols such as cetyl alcohol and oleyl achohol, and 2-hydroxyalkyl methyl ethers, etc. In some embodiments of a cosmetic composition, nonionic surfactants can be selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isosteareth-2, trideceth-3, hydroxystearic acid, propylene glycol stearate, PEG-2 stearate, PEG-100 stearate, sorbitan monostearate, glyceryl laurate, laureth-2, cocamide monoethanolamine, lauramide monoethanolamine, and mixtures thereof. In some embodiments, the cosmetic composition can comprise polysorbate 60.

In some embodiments, the surfactant can be in the form of a lamellar phase. It is proposed, without being limited by theory, that a lamellar phase can provide resistance to shear, adequate yield to suspend particles and droplets, desirable rheology characteristics, and/or long term stability. Therefore, lamellar compositions can be desirable, especially for suspending emollient and for providing consumer aesthetics. The lamellar phase tends to have a viscosity that minimizes the need for viscosity modifying agents, however, lamellar compositions can be more expensive and generally require more surfactant. As disclosed U.S. Pat. No. 5,952,286 to Kolodziej et al., herein incorporated by reference, certain liquid fatty acids (e.g., long chain, unsaturated and/or branched fatty acids); long chain, unsaturated and/or branched alcohols (e.g., oleyl alcohol or isostearyl alcohol) or derivatives (ester of fatty acids and ether of fatty acids) of these fatty acids and/or alcohols can be used in a typical rod-micellar solution and induce a lamellar phase. The lamellar phase surfactant also can comprise short chain saturated fatty acids such as capric acid and caprylic acid. Without being limited by theory, it is believed that the unsaturated part of the fatty acid of alcohol or the branched part of the fatty acid or alcohol acts to "disorder" the surfactant hydrophobic chains and induce formation of lamellar phase. Examples of suitable liquid fatty acids include oleic acid, isostearic acid, linoleic acid, linolenic acid, ricinoleic acid, elaidic acid, arichidonic acid, myristoleic acid, palmitoleic acid, and mixtures thereof. Examples of suitable ester derivatives include propylene glycol isostearate, propylene glycol oleate, glyceryl isostearate, glyceryl oleate, polyglyceryl diisostearate and mixtures thereof. Examples of alcohols include oleyl alcohol and isostearyl alcohol. Examples of ether derivatives include isosteareth or oleth carboxylic acid; or isosteareth or oleth alcohol. The structuring agent may be defined as having melting point below about 25° C. In a preferred embodiment, tobacco seed oil can provide the suitable liquid fatty acid (i.e., linoleic acid) necessary to induce a lamellar phase surfactant.

Non-limiting examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co.; and U.S. Pat. Nos. 3,929,678; 2,658,072; 2,438,091; 2,528,378; 2,658,072; 5,104,646 to Bolich Jr. et al., U.S. Pat. No. 5,106,609 to Bolich Jr. et al., each of which is herein incorporated by reference.

Compositions according to the present invention can comprise preservatives. Preservatives can be either synthetic or natural. In certain embodiments, preservatives can be used to inhibit growth of undesirable microorganisms. Natural preservatives can include black currant fruit extract, aspen bark, radish root, and sorbic acid, potassium sorbate, alone or in combination. Synthetic preservatives can include, for example, sodium hydroxymethylglycinate, tetrahexyldecyl ascorbate, tocopheryl acetate, phenoxyethanol, methylparaben, ethylparaben, propylparaben, imidazolidinyl urea, diazolidinyl urea, DMDM hydantoin, isothiazolinones, chlorinated aromatic compounds, para-hydroxybenzoic acids/parabens, alone or in combination. In various embodiments, the cosmetic composition can include disodium ethylenediaminetetraacetic acid (EDTA). It is believed that disodium EDTA can bind to metal ions and inactivate them, thereby preventing deterioration of the cosmetic product, protecting fragrance compounds, and preventing rancidity. Other natural and synthetic preservatives can be found in the Cosmetic Handbook and Personal Care Products Council ingredient information. When present in the cosmetic composition, one or more preservatives can be included in an amount from about 0.01% to about 20%, alternatively from about 0.1% to about 10%, alternatively from about 0.1% to about 5%, and alternatively from about 0.5% to about 3%, by weight of the composition.

In various embodiments, the cosmetic composition can comprise an additional component such as an anti-dandruff agent that is physically and chemically compatible with the essential components of the composition, for example. Examples of anti-dandruff agents include, but are not limited to, antimicrobial actives, pyridinethione salts, azoles, selenium sulfide, particulate sulfur, keratolytic acid, salicylic acid, octopirox (piroctone olamine), coal tar, and combinations thereof. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982, each of which is herein incorporated by reference. Other anti-dandruff agents can be found in the Cosmetic Handbook and Personal Care Products Council ingredient information. When present in the cosmetic composition, the anti-dandruff agent can be included in an amount from about 0.01% to about 5%, alternatively from about 0.1% to about 3%, and alternatively from about 0.3% to about 2%, by weight of the composition.

Various embodiments of the cosmetic composition can comprise one or more conditioning agents. Conditioning agents can include materials which are used to give a particular conditioning benefit to hair and/or skin. Conditioning agents useful in cosmetic compositions can comprise a water-insoluble, water-dispersible, non-volatile, liquid that forms emulsified, liquid particles. Non-limiting examples of conditioning agents include allantoin, xanthan gum, saturated methylene diphenyldiisocyanate (SMDI) copolymers (e.g., PPG-12/SMDI copolymer which is a copolymer of PPG-12 and SMDI monomers), materials characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in an aqueous surfactant matrix. Other conditioning agents can be found in the Cosmetic Handbook and Personal Care Products Council ingredient information. When present in the cosmetic composition, the conditioning agent can be included in an amount from about 0.01% to about 10%, alternatively from about 1.0% to about 5%, and alternatively from about 0.01% to about 1%, by weight of the composition.

Some embodiments of cosmetic compositions can comprise a suspending agent. The suspending agent can be present at concentrations effective for suspending water-insoluble material in dispersed form in the cosmetic composition. In some embodiments, the suspending agent can be present at concentrations effective for modifying the viscosity of the cosmetic composition as desired for the final cosmetic product. Such concentrations can range from about 0.1% to about 10% or about 0.5% to about 5.0% by weight of the composition. Suspending agents useful in the present invention include, for example, crystalline suspending agents which can be categorized as acyl derivatives, long chain amine oxides, and mixtures thereof. Examples of such suspending agents are described in U.S. Pat. No. 4,741,855, herein incorporated by reference in its entirety. Suspending agents can also include, for example, ethylene glycol esters of fatty acids having from about 16 to about 22 carbon atoms, ethylene glycol stearates, mono and distearate, distearate containing less than about 7% of the mono stearate, and combinations thereof. Other suspending agents can be found in the Cosmetic Handbook and Personal Care Products Council ingredient information.

Various embodiments of cosmetic compositions can comprise at least one humectant. A humectant can function, for example, to attract and retain moisture in the air by absorption. A humectants can be considered, for example, a substance that can be used to keep things moist. Humectants useful in cosmetic compositions of the present invention can be selected from the group consisting of polyhydric alcohols, water soluble alkoxylated nonionic polymers, and mixtures thereof. Non-limiting examples of humectants that can be used in cosmetic compositions include acetyl tetrapeptide-5, acetamide MEA, agarose, ammonium lactate, arginine PCA, betaine, butylene glycol, copper PCA, corn glycerides, diglycereth-7 malate, diglycerin, dimethyl imidazolidinone, erythritol, gelatin, glycose, glycuroinc acid, glycuronolactone, glutamic acid, glycereth-12, glycerin, honey extract, hylauronic acid, hydroloyzed wheat starch, hydroxyethyl sorbitol, lactamide, lactic acid, maititil, melibiose, panthenol, pantolactone, PCA, polyglycuronic acid, polyglycerylmethacrylate, propylene glycerol, saccharide hydrolysate, sea salt, seasame amino acids, sodium aspartate, sodium lactate, sodium malate, sodium PCA, sodium polyaspartate, sorbitol, TEA-lactate, triglycereth-7 citrate, urea, xylose, *Glycyrrhiza glabra* (Licorice) root extract and combinations thereof. Other humectants can be found in the Cosmetic Handbook and Personal Care Products Council ingredient information. The humectants can be present in an amount by weight of the composition from about 0.1% to about 20%, or from about 0.1% to about 10%, and alternatively from about 0.5% to about 5%.

Various embodiments of cosmetic compositions can comprise an occlusive component. It is believed, without being limited by theory, that occlusives can increase the water content of the skin by slowing the evaporation of water from the surface of the skin. In certain embodiments, occlusives can be greasy and can be most effective when applied to damp skin. In various embodiments, an occlusive component comprises mineral oil. However, in some embodiments, mineral oil can be less effective at preventing evaporation of water than other occlusives. In some embodiments, an occlusive component comprises lanolin. However, lanolin can be expensive and potentially irritating. In some embodiments, an occlusive component comprises at least one silicone derivative (e.g., dimethicone and cyclomethicone). In certain embodiments, silicone derivatives can be less greasy, but they can also have a limited moisturizing effect. Non-limiting examples of occlusives useful in cosmetic compositions include acetylated castor oil, acetylated lanolin alcohol, behenyl isostearate, beeswax, C12-18 acid triglyceride, C20-40 alcohols, C20-40 alkyl dimethicone, C16-36 alkyl stearate, C18-70 isoparaffin, C20-24 olefin, C10-18 triglycerides, candelilla, canola oil, caprylic/capric triglyceride, carnauba, cetearyl methicone, cetyl ricinoleate, cholesteryl oleate, cyclomethicone, decyl myristate, dimethicone, distearyl ether, glycol dioleate, hexyldecyl isostearate, hydrogenated castor oil, hydrogenated lanolin, isocetyl myristate, lanolin linoleate, lauryl cocoate, lecithin, mineral oil, myristyl myristate, neatsfool oil, octyldodecyl stearate, oleyl linoleate, palm kernel wax, paraffin, pentaerythrityl tetracocoate, petroleum, propylene glycol dioleate, shark liver oil, soybean lipid, stearyl stearate, squalane, tall oil, tocopherol, trihexyldecyl citrate, triisostearin, vegetable oil, and combinations thereof. Other occlusives can be found in the Cosmetic Handbook and Personal Care Products Council ingredient information. In some embodiments, occlusives can be present at concentrations effective for modifying the cosmetic composition as desired for the final cosmetic product. Such concentrations can range from about 0.1% to about 10% or about 0.5% to about 5.0% by weight of the composition, for example.

In various embodiments of cosmetic compositions, the composition can comprise an emollient. In various embodiments, emollients can act as lubricants and thereby help maintain the soft, smooth and pliable appearance of skin and/or hair. Non-limiting examples of emollients useful in cosmetic compositions include acetylated lanolin, acetyl trihexyl citrate, avocado sterois, butyl myristate, C14-15 alcohols, C12-13 alkyl ethylhexanoate, caprylyl glycol, castor oil, cetyl acetate, cetyl oleate, C14-16 glycol palmitate, C12-20 isoparaffin, C12-15 alkyl benzoate, cyclomethicone, decyl oleate, diethylhexyl adipate, diethylhexyl malate, diisodecyl adipate, diisopropyl dilinoleate, dimethicone copolyol, dipropyl adipate, ethylhexyl palmitate, ethyl linoleate, glyceryl dioleate, glyceryl ricinoleate, glyceryl stearates, glycol palmitate, glycol stearate, hexyl laurate, isocetyl alcohol, isodecyl stearate, isohexyl palmitate, isopropyl isostearate, isopropyl myristate, isopropyl palmitate, isostearyl alcohol, jojoba oil, lanolin, methyl palmitate, myristyl propionate, octyl octanoate, octyl stearate, PEG-4 lanolate, PEG-5 tristearyl citrate, polyglyceryl-6 oleate, plyglycerol-2 triisostearate, PPG-20 cetyl ether, PPG-4 laureth-2, propylene glycol linoleate, sodium hyaluronate, squalene, sucrose oleate, sunflower seed oil glycerides, tall oil glycerides, tridecyl stearate, wheat germ glycerides, *Glycyrrhiza glabra* (Licorice) root extract, aloe barbadensis leaf juice, and combinations thereof. Other emollients can be found in the Cosmetic Handbook and Personal Care Products Council ingredient information. When present in the cosmetic composition, one or more emollients can be included in an amount from about 0.01% to about 20%, alternatively from about 0.1% to about 10%, and alternatively from about 0.5% to about 5%, by weight of the composition.

In various embodiments, pigments can be used to provide color to the final cosmetic composition. Pigments can be synthetic or natural. Natural pigments can include pigments or plant-derived colors, for example. Natural pigments can be inorganic (mineral) or organic, white or non-white, and coated or uncoated particles, for example. Natural pigments can include, for example, cerium oxide, iron oxide, titanium dioxide, zinc oxide, zirconium oxide, carbon black, manganese violet, ultramarine blue, D&C and FD&C colors, azo, indigoid, insoluble metallic salts of certified color additives, and the like, and mixtures thereof. Other pigments can be found in the Cosmetic Handbook and Personal Care Products Council ingredient information. When present in the cosmetic composition, pigments can be included in an amount from about 0.01% to about 5%, alternatively from about 0.1% to about 3%, and alternatively from about 0.1% to about 2%, by weight of the composition.

Some embodiments of cosmetic compositions can include additional ingredients useful for treating skin and/or hair. For example, some embodiments comprise cholecalciferol (also referred to as vitamin $D_3$). Cosmetic compositions can comprise coenzyme Q10, pomegranate (punica gradatum) extract, and lipoic acid, either alone or in combination, for example. In certain embodiments, these agents can function as an antioxidant, for example. Embodiments of a cosmetic composition can comprise cholecalciferol. Cholecalciferol can function as an antioxidant and anti-inflammatory agent, for example. Cosmetic compositions can comprise witch hazel extract. In some embodiments, witch hazel extract is useful as an anti-inflammatory agent, for example. Some embodiments of cosmetic compositions can comprise palmitoyl pentapeptide-4, PEG-8 oligopeptide, green tea extract, palmityol tetrapeptide-7, hesperidin methylchalcone, steareth-20-dipeptide-2, and combinations thereof. Palmitoyl pentapeptide-4 can function, for example, as a skin rejuvenation, anti-wrinkle compound. In some embodiments, PEG-8 oligopeptide can be useful for treating wrinkles. Green tea extract can function, for example, as an antioxidant that can provide anti-aging benefits in cosmetic compositions. In some embodiments, palmitoyl tetrapeptide-7 can be useful in reducing the appearance of fine lines and wrinkles by enhancing collagen and hyaluronic acid production. In certain embodiments, hesperidin methylchalcone can be useful in reducing dark circles under the eye. Steareth-20-dipeptide-2 is another compound that can function to reduce dark circles under the eye, for example. Certain embodiments of cosmetic compositions comprise polyacrylamide. Polyacrylamide can, for example, dry to form a thin coating on skin or hair, thereby helping hair hold style by inhibiting the hairs ability to absorb moisture and helping retain skin products on the skin after immersion in water (e.g., sunscreen). When present in a cosmetic composition, each of these additional ingredients can be present in an amount of about 0.01% to about 5%, alternatively from about 0.1% to about 3%, and alternatively from about 0.1% to about 1%, by weight of the composition.

Hair Treatment Products

Shampoo is a hair care product that can be used for the removal of oils, dirt, skin particles, dandruff, environmental pollutants and other contaminant particles that gradually build up in hair. Many modern shampoos further include a conditioning component used to smooth and detangle hair that has been washed with shampoo. Common ingredients found in hair care products include vitamins and provitamins, botanical extracts, a UV protectant, fruit acids or alpha-hydroxy acids, antioxidants, water, humectants, a surfactant (also referred to as a detergent), an emulsifier, preservatives, solvents, and combinations thereof. Examples of common detergent-type ingredients useful in a shampoo composition include ammonium lauryl sulfate, sodium laureth sulfate (derived from coconut oils and can be useful, for example, to soften water and create a lather), sodium lauroamphoacetate (derived from coconut oils and can be useful, for example, as a cleanser and a counter-irritant), and sodium lauryl sulfate. Other surfactants that can be useful in a shampoo composition include, for example, cocamideopropyl betaine, glycol, polysorbate 20 (PEG(20)) (can be useful, for example, to solubilize fragrance oils and essential oils), and polysorbate 80 (PEG(80)) (can be useful, for example, to emulsify oils in water). In addition, thickeners can be useful in shampoo compositions. PEG-150 distearate is an example of a thickener that can be used in hair treatment compositions. In various compositions, sodium chloride can be used as a thickener if the main surfactants are sodium lauryl sulfates. In various compositions, ammonium chloride can be used to thicken the composition if the surfactants are ammonium based. Examples of conditioning-type components that can be useful in hair treatment products include guar hydroxypropyltrimonium chloride, dimethicone, silicone, and polyquaternium-10. Examples of preservatives useful in shampoo compositions include citric acid, quaternium-15 and methylisothiazolinone (MIT).

As discussed above, a tobacco seed extract can also provide an advantageous source of linoleic acid in cosmetic products. Tobacco seed oil can replace the oil components conventionally used in hair treatment products. The high concentration of linoleic acid of the tobacco seed oil can provide beneficial effects on skin and hair, and can also function as an effective and efficient emollient and/or surfactant in hair treatment composition. Furthermore, the resulting compositions incorporating tobacco seed oil are found to have the same sensory characteristics and general appearance has traditional hair treatment products incorporating emollients and surfactants known in the art.

As described in U.S. Appl. Pub. No. 2013/0090279, herein incorporated by reference in its entirety, a detersive surfactant may be selected from an anionic detersive surfactant, zwitterionic, or an amphoteric detersive surfactant, or a combination thereof. Suitable anionic surfactant components for use in the composition herein include those which are known for use in hair care or other personal care shampoo compositions. In one embodiment, the anionic surfactant may be a combination of sodium lauryl sulfate and sodium laureth-n sulfate, for example. The concentration of the anionic surfactant component in the shampoo should be sufficient to provide the desired cleaning and lather performance, and generally ranges from about 2% to about 50%, from about 8% to about 30%, from about 10% to about 25%, or from about 12% to about 22%. Suitable amphoteric or zwitterionic detersive surfactants for use in a hair treatment composition include those which are known for use in hair care or other personal care cleansing. Concentrations of such amphoteric or zwitterionic detersive surfactants can range from about 0.5% to about 20%, alternatively from about 1% to about 10%. Non-limiting examples of suitable zwitterionic or amphoteric surfactants are described above.

Various embodiments of hair treatment compositions further include lather builders. In some embodiments, lather builders, or co-surfactants, can comprise materials which are combined with the undecyl sulfate surfactant and optionally anionic surfactants to enhance lather volume and/or to modify lather texture. Lather builders can serve to produce faster lather, facilitate easier rinsing, and/or mitigate harshness on the keratinous tissue. They can further aid in producing lather having a more desirable texture, volume and/or other properties. These materials can be selected from a variety of families of structures including, but not limited to, amphoteric, zwitterionic, cationic, and nonionic surfactants. These chemical compounds can help create the suds, which can help the detergents to work better by allowing more dirt to be lifted from the hair and washed away. They can be used with anionic surfactants in a weight ratio of 1:20 to 1:4, and alternatively in the 1:12 to 1:7 weight ratio. Embodiments of hair treatment compositions of the present invention may comprise from about 0.5 wt % to about 10 wt %, alternatively from about 0.5 wt % to about 5 wt %, alternatively from about 0.5 wt % to about 3 wt %, alternatively from about 0.5 wt % to about 2 wt %, and alternatively from about 0.5 wt % to about 1.75 wt % by weight of the composition of at least one suitable lather builder. In some embodiments, lather builders incorporated in shampoo or other cleansing cosmetic compositions comprise cocamide mea, lauramide diethanolamide and/or cocamidopropyl betaine, for example.

Many detergents are alkaline or base, which can make the hair look dull. Various embodiments of hair treatment products can include acids. Acids can function to keep the hair looking shiny, for example. Commonly used acids in shampoos include ascorbic acids and citric acid, for example. Collagen (e.g., hydrolyzed collagen) can also be included in certain hair treatment compositions. Collagen can, for example, enhance the hair body, suppleness and/or sheen of the hair.

Many hair treatment compositions also include thickening agents. Thickeners can ensure that the product is thick and creamy, for example. In various embodiments of hair treatment products, thickeners include xanthan gum, cetyl alcohol, sodium chloride, and stearyl alcohol. Many of these chemical compounds further act as conditioning agents on the hair. Some embodiments of hair treatment compositions comprise other conditioners such as allantoin and glycerin, for example.

Specialty shampoos, such as baby shampoo, curling shampoo, dandruff shampoo, and other types of shampoos can comprise additional additives. Various embodiments of shampoo compositions further comprise components that provide ultraviolet light protection, proteins, vitamins, plant extracts, other organic ingredients, and combinations thereof. In an embodiment, a sunscreen component used in a hair treatment composition can be octyl salicylate and/or PABA, a compound found in various sunscreen lotions.

Various embodiments of hair treatment compositions can comprise hydrophobic moisturizing materials selected from the group consisting of petrolatum, lanolin, hydrocarbon oils such as mineral oil, natural and synthetic waxes such as microcrystalline waxes, paraffins, ozokerite, lanolin wax, lanolin alcohols, lanolin fatty acids, polyethylene, polybutene, polydecene and perhydrosqualene, volatile or non-volatile organosiloxanes and their derivatives such as dimethicones, cyclomethicones, alkyl siloxanes, polymethylsiloxanes and methylphenylpolysiloxanes, lanolin oil, esters such as isopropyl lanolate, acetylated lanolin, acetylated lanolin alcohols, lanolin alcohol linoleate, lanolin alcohol riconoleate natural and synthetic triglycerides such as castor oil, soy bean oil, sunflower seed oil, maleated soy bean oil, safflower oil, cotton seed oil, corn oil, walnut oil, peanut oil, olive oil, cod liver oil, almond oil, avocado oil, palm oil and sesame oil, castor oil derivatives, sefoses, and combinations thereof. As discussed above, essential oils useful in cosmetic compositions can beneficially comprise tobacco seed oil. Essential oils can, for example, increase the effectiveness of hair treatment compositions.

Cleansers

Body and facial cleansers can be designed to clear away dirt and grime from the skin. Many cleansers can also serve to moisturize the skin, sooth irritated skin, reduce the signs of aging or repair damaged facial skin. Many cleansers contain similar basic ingredients. A tobacco seed extract can provide an advantageous source of linoleic acid by replacing, for example, an oil component, an emollient, an anti-aging agent, and/or a surfactant in cleansing products. The high concentration of linoleic acid of the tobacco seed oil can provide beneficial effects on skin, particularly when dealing with problems such as acne, dryness, and swelling. In certain embodiments, cleansing products incorporating tobacco seed oil can provide an antioxidant and an anti-inflammatory effect, and the tobacco seed oil can further function as an emollient and/or surfactant. Furthermore, the resulting compositions incorporating tobacco seed oil are generally found to have the same or similar sensory characteristics and appearance as traditional cleansing products incorporating for example, oils, anti-aging agents, emollients and surfactants known in the art.

In general, cleansers comprise some form of surfactant (i.e., a soap or detergent). Facial cleansers tend to be milder on the skin because the surfactant they contain is milder than that of body cleansers. Some liquid body cleansers can incorporate moisturizing agents to compensate for a harsher surfactant used. The moisturizing agent can comprise emollients, such as linoleic acid, for example. Cleansers for the skin can generally be divided into three main types: foaming cleansers, non-foaming cleansers and abrasive scrubs.

Foaming cleansers can provide a pleasing feel because in certain embodiments, they lather and leave behind a refreshing sensation after they are rinsed off. Foaming facial cleansers can include, for example, lotions, creams, gels, self-foaming cleansers, arerosols, scrubs, etc.

Non-foaming cleansers can be a mild type of cleanser. In certain embodiments, non-foaming cleansers contain small amounts of surfactant and can be wiped off instead of rinsed off. In some embodiments, non-foaming cleansers are not intended to come in contact with water, and thereby they can deposit more of the helpful ingredients onto the skin. Non-foaming cleansers can include creams, lotions (sometimes referred to as milks), and cold creams.

Abrasive scrubs can contain ingredients that physically scrub the skin to help remove dead skin cells, thereby leaving the skin smoother. However, the granules that do the actual scrubbing can cause irritation, redness, and even tiny cuts on the face. Therefore, it can be advantageous to incorporate a moisturizing agent into the abrasive scrub. Non-limiting examples of exfoliating granules include sodium tetraborate decahydrate granules, polyethylene silica or beads, jojoba esters, cross-linked polymethacrylate, calcium carbonate, ground seeds (e.g., apricot, almond and walnut seeds), aluminum oxide and combinations thereof.

Skin Treatment Products

Skin in general is composed of three distinct layers: the outer protective straum coreum; the middle epidermis layer and the inner dermis layer. Sweat glands and hair roots are found in the dermis layer. As discussed above, a tobacco seed extract can replace components conventionally used in cosmetic products. The high concentration of linoleic acid of the tobacco seed oil can provide beneficial effects on skin, particularly when dealing with problems such as acne, dryness, and swelling. In certain embodiments, cosmetic products incorporating tobacco seed oil can also be effective emollients, antioxidant and anti-inflammatory agents. Furthermore, the resulting compositions incorporating tobacco seed oil are found to have the same sensory characteristics and general appearance has traditional skin treatment products incorporating for example, anti-aging agents, emollients and anti-inflammatory agents known in the art.

In various embodiments of cosmetic compositions intended for use on the skin, the composition can comprise a cosmetically or dermatologically acceptable medium or base. The composition can be provided in the form of any topically applicable formulations, for example, a solution, a gel, a solid, an anhydrous paste, an oil-in-water emulsion, a suspension, a micro emulsion, a microcapsule, a micro granule, an ionic (liposome) or nonionic vesicular dispersion, a cream, a skin lotion, a milk lotion, a powder, an ointment, a spray or a conceal stick. These compositions can be prepared according to any convention method known in the art.

The composition for skin application according to the present invention can contain additives commonly used in the cosmetic or dermatological field, for example, fat, an organic solvent, a solubilizing agent, a concentrating agent, a gelling agent, a softener, an antioxidant, a suspending agent, a stabilizer, a foaming agent, an aromatic, a surfactant, water, an ionic or non-ionic emulsifier, a filler, a metal ion sequestering agent, a chelating agent, a preservative, vitamins, a blocking agent, a wetting agent, essential oil, dyes, pigments, a hydrophilic or lipophilic activator, lipid vesicles, or the like. These additives may be included in an amount commonly used in the cosmetic or dermatological field.

A lotion can be a low to medium viscosity topical preparation intended for application to unbroken skin. Creams and gels can have higher viscosity. Many lotions and creams are intended to smooth, re-hydrate, and soften the skin. Categories of ingredients useful in skin moisturizers can include: humectants, emollients and preservatives. Humectants, such as urea, glycerin, and alpha hydroxyl acids, can help absorb moisture from the air and hold it in the skin, for example. Emollients, such as lanolin, mineral oil and petrolatum, can help fill in spaces between skin cells, lubricating and smoothing the skin, for example. Preservatives can help prevent bacteria grown in moisturizers. Other ingredients can include vitamins, minerals, plant extracts, and fragrances, for example.

In various embodiments, humectants can attract water from the dermis into the epidermis, increasing the water content in the epidermis. It is believed, without being limited by theory, that humectants can also attract water from the atmosphere into the epidermis. In various embodiments of body and facial moisturizing compositions, a humectant component can comprise ammonium lactate, butylene glycol, propylene glycerol, glycerin, hylauronic acid, sodium pyrrolidone carboxylic acid (PCA), sorbitol, urea, and combinations thereof. Humectants, for example glycerin, can provide smoother-looking skin.

Emollients can be ingredients that can remain in the stratum coreum to act as lubricants. In various embodiments, emollients can help maintain the soft, smooth, and pliable appearance of the skin. Emollients can be oil-based or water-based. Oil-based emollients can be heavier and may leave a residue on skin, and therefore these can be beneficial for dry skin that requires intense moisturizing, for example. Water-based emollients can be lighter and less greasy, which can make them ideal for normal, oily or acne-prone skin. In various embodiments of moisturizing compositions, an emollient can comprise cyclomethicone, dimethicone copolyol, glyceryl stearates, propylene glycol linoleate, isopropyl palmitate, lanolin, and combinations thereof. As discussed above, emollients useful in cosmetic compositions can comprise tobacco seed oil. Tobacco seed oil can provide a relatively high percentage of linoleic acid, which can have beneficial effects on skin as discussed above.

Additional ingredients can be added to moisturizers to create a special effect on the skin such as enhancing the appearance of dry or damaged skin. Chemicals that slow oxidation by reacting with free radicals include tocopherols and ascorbic acid, for example. It is proposed, without being limited by theory, that although citric acid, tartaric acid, and EDTA may not have strong antioxidating properties, they can enhance the antioxidant effects of other ingredients. As discussed above, linoleic acid has many beneficial properties in a variety of moisturizing compositions.

Various embodiments of cosmetic products can be intended to treat undesirable facial lines, wrinkles, and/or dark circles under the eyes. Embodiments of this type of cosmetic composition can comprise one or more of three ingredients: retinol, Vitamin K and Vitamin C.

Retinol and/or retinyl palmitate (ester of retinol and palmitic acid) can each be useful as an anti-wrinkle agent. It is believed to be able to greatly reduce the fine lines and wrinkles that appear around they eye, for example. Retinol is a biological form of Vitamin A. Without being limited by theory, Retinol is believed to be able to even out the skin's complexion and make the skin appear more luminous. It is also thought that Retinol can penetrate the outermost layers of the skin's surface, getting underneath to plump up and brighten the dermal layer. Furthermore, retinol is believed to also function as an antioxidant and promote new skin cell growth. Therefore, it is thought of as an efficient and effective wrinkle reducer, fine line eraser and pigmentation stabilizer. However, retinol is frequently associated with consumer discomfort characterized by burning, stinging, itching or sensation of tightness after application. Therefore, linoleic acid can be a good substitute for an anti-wrinkle agent in cosmetic compositions, as discussed above.

It is proposed, without being limited by theory, that Vitamin K, also known as Phytonadione, can enhance collagen development in the skin, thus plumping up the area under the eyes and decreasing dark circles. It is thought that Vitamin K can also help with increased blood circulation which can enhance skin appearance. It can renew damaged skin, for example damage from the sun's rays, lack of sleep, genetics, aging or other causes. Vitamin K can improve the strength of these blood vessel walls, making them less visible underneath the skin (e.g., reducing dark circles under the eyes).

It is proposed, without being limited by theory, that Vitamin C, or ascorbic acid, also aids in strengthening the walls of these blood vessels. It is believed that an added benefit of Vitamin C for dark circles and lines under the eyes is an increase in collagen or plumping of the under-eye area. It is further proposed that Vitamin C can be used to defuse free radicals and counterbalance the negative effects of exposure to UV rays. A lightening of the skin can be provided with the use of Vitamin C as an ingredient in eye cream compositions. In some embodiments, tetrahexyldecyl ascorbate, a stable, oil-soluble Vitamin C ester which can have antioxidant activity, for example, can be included in the cosmetic composition.

EXPERIMENTAL

Aspects of the present invention are more fully illustrated by the following examples, which are set forth to illustrate certain aspects of the present invention and is not to be construed as limiting thereof.

Example 1

The following non-limiting example describes how tobacco seed oil can be extracted and refined for purposes of the invention.

Tobacco seeds are harvested from field grown plants and extracted with hexane and agitation. The defatted seed cake is removed from the hexane extract by simple filtration. The extract is then placed in a distillation apparatus, which separates the hexane from the tobacco seed oil.

The raw oil derived from these processes comprises approximately 20% by weight free fatty acids, and 80% by weight triglyceride bound fatty acids, comprising primarily linoleic acid (~70% by weight). The free fatty acids are then removed by a refinement process that consists of an acidic wash (citric acid) followed by a base wash (sodium hydroxide) and subsequent centrifugation. The resulting refined oil is approximately 4% by weight free fatty acids and 96% triglyceride bound fatty acids. A lower free fatty acid content is advantageous for product incorporation as free fatty acids are subject to oxidation and eventual rancidity.

Example 2

Storage and stability testing is performed on various embodiments of cosmetic products incorporating tobacco seed oil. The incorporation of the tobacco seed oil does not pose any unusual problems or issues when preparing formulations. The material is relatively easy to incorporate and is essentially comparable to Argan oil.

Stability testing (e.g., testing at 45° C., Freeze/thaw testing, testing at 4° C. and testing at room temperature) does not show any color or odor issues and no noticeable adverse effect on product integrity. Argan oil and tobacco seed oil behave in similar manners. The odor of the tobacco seed oil is very low and does not appear to go "rancid" or adversely affect the formulations prepared under stability test conditions.

In a Shampoo/Body Wash formula, the tobacco seed oil does not appear to have any adverse effect on foaming as compared to the Argan oil. From a practical use assessment, there does not appear to be any major formulation challenges that would prevent use of tobacco seed oil in skin care and hair care formulations.

Example 3

As shown in Table 1, tobacco seed oil is incorporated into a facial moisturizer. The tobacco seed oil replaces sunflower seed oil, olive oil and grape seed oil in the product composition. The resulting product has sensory characteristics similar to the characteristics of a comparable composition containing the replaced ingredients.

TABLE 1

Night Facial Moisturizer

| Ingredient Name | Weight % |
|---|---|
| Deionized Water | 20-80 |
| Tobacco Seed Oil | 1-5 |
| *Aloe Barbadensis* Leaf Juice | 2-5 |
| Glycerin | 2-5 |
| Stearic Acid | 0-5 |
| Glyceryl Stearate | 0-5 |
| *Glycyrrhiza Glabra* (Licorice) Root Extract | 0-5 |
| *Butyrospermum Parkii* (Shea Butter) | 0-5 |
| Phenoxyethanol | 0-5 |
| Sodium Hyaluronate | 0-5 |
| Carbomer | 0-5 |
| Cetyl Alcohol | 0-5 |
| Collagen | 0-5 |
| Isodecyl Neopentanoate | 0-5 |
| Panthenol | 0-5 |
| Triethanolamine | 0-5 |
| C12-15 Alkyl Benzoate | 0-5 |
| Tetrahexyldecyl Ascorbate | 0-2 |
| Tocopheryl Acetate | 0-2 |
| Bergamot Extract | 0-3 |
| Disodium EDTA | 0-1 |
| Retinyl Palmitate | 0-1 |
| Cholecalciferol | 0-1 |
| Allantoin | 0-1 |

Example 4

As shown in Table 2, tobacco seed oil is incorporated into an anti-aging cream with Matrixyl® which is a brand of an anti-wrinkle active ingredient. The tobacco seed oil replaces caprylic/capric triglyceride in the product composition. The resulting product has sensory characteristics similar to the characteristics of a comparable composition containing the replaced ingredient.

TABLE 2

Anti-Aging Cream

| Ingredient Name | Weight % |
|---|---|
| Deionized Water | 20-80 |
| Tobacco Seed Oil | 1-5 |
| Witch Hazel Extract | 1-5 |
| Glycerol Stearate | 1-5 |
| PEG-100 Stearate | 1-5 |
| Glycerin | 1-5 |
| Butylene Glycol | 1-5 |
| Carbomer | 1-5 |
| Polysorbate 20 | 1-5 |
| Palmitoyl Pentapeptide-4 (Matrixyl ®) | 1-5 |
| Shea Butter | 1-5 |
| Glyceryl Polymethacrylate | 1-5 |
| PEG 8 Oligopeptide | 1-5 |
| Phenoxyethanol | 1-5 |
| Caprylyl Glycol | 1-5 |
| Sorbic Acid | 1-5 |
| Ammonium Acryloyldimethyltaurate VP Copolymer | 1-5 |
| Cetearyl Olivate | 1-5 |
| Sorbitan Olivate | 1-5 |
| PPG-12 | 1-5 |
| SMDI/Copolymer | 1-5 |
| Sodium Hyaluronate | 1-5 |
| Tocopheryl Acetate | 1-5 |
| Disodium EDTA | 1-5 |
| Xanthan Gum | 1-5 |
| Peppermint Oil | 1-5 |
| Green Tea Extract | 1-5 |
| Tetrahexyldecyl Ascorbate | 1-5 |

Example 5

As shown in Table 3, tobacco seed oil is incorporated into a facial and body cream composition. The tobacco seed oil replaces caprylic/capric triglyceride in the product composition. The resulting product has sensory characteristics similar to the characteristics of a comparable composition containing the replaced ingredient.

TABLE 3

Head to Toe Face and Body Cream

| Ingredient Name | Weight % |
| --- | --- |
| Deionized Water | 20-80 |
| Tobacco Seed Oil | 1-5 |
| Polyacrylamide | 1-5 |
| C 13-14 Isoparaffin | 1-5 |
| Laureth-7 | 1-5 |
| Glycerin | 1-5 |
| *Aloe Barbadensis* Leaf Juice | 1-5 |
| Isodecyl Neopentanoate | 1-5 |
| Phenoxyethanol | 1-5 |
| Potassium Sorbate | 1-5 |
| Tocopheryl Acetate | 1-5 |
| Fragrance | 0-2 |

Example 6

As shown in Table 4, tobacco seed oil is incorporated into an eye serum composition. The tobacco seed oil replaces caprylic/capric triglyceride in the product composition. The resulting product has sensory characteristics similar to the characteristics of a comparable composition containing the replaced ingredient.

TABLE 4

Green Apple Eye Serum

| Ingredient Name | Weight % |
| --- | --- |
| Deionized Water | 20-80 |
| Tobacco Seed Oil | 1-5 |
| Glycerin | 1-5 |
| *Aloe Barbadensis* Leaf Juice | 1-5 |
| Phenoxyethanol | 1-5 |
| Acetyl Tetrapeptide-5 | 1-5 |
| Hesperidin Methylchalcone | 1-5 |
| Steareth-20-Dipeptide-2 | 1-5 |
| Palmitoyl Tetrapeptide-7 | 1-5 |
| Carbomer | 1-5 |
| Fragrance | 1-5 |
| Lecithin | 1-5 |
| Alcohol | 1-5 |
| Lipoic Acid | 1-5 |
| Tocopheryl Acetate | 1-5 |
| Potassium Sorbate | 1-5 |
| Coenzyme Q10 | 1-5 |
| Sodium Hydroxide | 1-5 |
| Retinyl Palmitate | 1-5 |
| Cholecalciferol | 1-5 |

Example 7

As shown in Table 5, tobacco seed oil is incorporated into a facial cleansing cream composition. The tobacco seed oil replaces caprylic/capric triglyceride in the product composition. The resulting product has sensory characteristics similar to the characteristics of a comparable composition containing the replaced ingredient.

TABLE 5

Cleansing Cream

| Ingredient Name | Weight % |
| --- | --- |
| Deionized Water | 20-80 |
| Tobacco Seed Oil | 1-5 |
| Sodium C14-16 Olefin Sulfonate | 1-5 |
| Cocamidopropyl Betaine | 1-5 |
| Glycerin | 1-5 |
| Witch Hazel Extract | 1-5 |
| Lauramide Diethanolamide | 1-5 |
| Glyceryl Stearate | 1-5 |
| Polysorbate 60 | 1-5 |
| Stearic Acid | 1-5 |
| Cetyl Alcohol | 1-5 |
| Shea Butter | 1-5 |
| Phenoxyethanol | 1-5 |
| Caprylyl Glycol | 1-5 |
| Sorbic Acid | 1-5 |
| Sodium Hydroxymethylglycinate | 1-5 |
| Carbomer | 1-5 |
| Potassium Sorbate | 1-5 |

Example 8

As shown in Table 6, tobacco seed oil is incorporated into a body butter composition. The tobacco seed oil replace sunflower seed oil, almond oil, avocado oil and pumpkin seed oil in the product composition. The resulting product has sensory characteristics similar to the characteristics of a comparable composition containing the replaced ingredients.

TABLE 6

Pomegranate and Acai Body Butter

| Ingredient Name | Weight % |
| --- | --- |
| Deionized Water | 20-80 |
| Tobacco Seed Oil | 1-5 |
| Cetearyl Alcohol | 1-5 |
| Shea Butter | 1-5 |
| Glycerin | 1-5 |
| *Aloe Barbadensis* Leaf Juice | 1-5 |
| Stearic Acid | 1-5 |
| Phenoxyethanol | 1-5 |
| Caprylyl Glycol | 1-5 |
| Sorbic Acid | 1-5 |
| Cetyl Alcohol | 1-5 |
| Carbomer | 1-5 |
| Pomegranate (*Punica Gradatum*) Extract | 1-5 |
| Fragrance | 1-5 |
| Panthenol | 1-5 |
| Tocopheryl Acetate | 1-5 |
| Retinyl Palmitate | 1-5 |
| Cholecalciferol | 1-5 |

Example 9

As shown in Table 7, tobacco seed oil is incorporated into a hair cleansing composition. The tobacco seed oil replaces caprylic/capric triglyceride in the product composition. The resulting product has sensory characteristics similar to the characteristics of a comparable composition containing the replaced ingredient.

TABLE 7

Shampoo

| Ingredient Name | Weight % |
| --- | --- |
| Deionized Water | 20-80 |
| Sodium Lauryl Sulfate | 25-35 |
| Cocamideopropyl Betaine | 10-25 |
| Sodium Laureth Sulfate | 1-10 |
| Tobacco Seed Oil | 1-10 |
| Ammonium Chloride | 1-5 |
| Citric Acid | 0-5 |
| EDTA | 0-5 |
| Sodium Chloride | 0-5 |
| Fragrance | 0-5 |
| Polysorbate 20 | 0-5 |
| DMDM Hydantoin | 0-5 |

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A method of forming a cosmetic composition, comprising:
   receiving a crude oil that has been extracted from a seed of a plant of the *Nicotiana* species;
   refining the crude oil through a chemical modification process comprising: treating the crude oil that has been extracted from a seed of the plant of the *Nicotiana* species with an acid to give an acid-treated oil; neutralizing the acid treated oil with a basic solution to give a neutralized mixture; and separating a precipitate from the neutralized mixture to provide the refined tobacco seed oil; and
   incorporating the refined tobacco seed oil into a cosmetic composition comprising the refined tobacco seed oil and at least one cosmetically acceptable carrier, wherein the cosmetic composition is in a form adapted for application to skin or hair;
   wherein the refined tobacco seed oil has a free fatty acid content of less than about 15 weight percent, based on the total weight of the refined tobacco seed oil.

2. The method of claim 1, wherein the acid is citric acid.

3. The method of claim 1, wherein the basic aqueous solution is sodium hydroxide.

4. The method of claim 1, further comprising receiving a seed of the plant of the *Nicotiana* species and extracting the crude oil by dissolving the seed in a solvent suitable to extract the crude oil to form a solution and a residual solid seed material, separating the solution from the residual solid seed material, and concentrating the solution to provide an extracted or leached crude oil.

5. The method of claim 1, wherein the refined tobacco seed oil has a free fatty acid content of less than about 10 weight percent, based on the total weight of the refined tobacco seed oil.

6. The method of claim 1, wherein the refined tobacco seed oil comprises at least about 60 weight percent of linoleic acid, based on the total weight of the refined tobacco seed oil.

7. The method of claim 1, wherein the cosmetic composition is in the form of an emulsion with an aqueous phase and an oily phase comprising the tobacco seed oil.

8. The method of claim 1, wherein the cosmetically acceptable carrier is an aqueous carrier and the composition is in the form of an emulsion.

9. The method of claim 1, wherein the cosmetic composition is in the form of a liquid, a lotion, a gel, a cream, a milk, an ointment, a paste, a plaster, a powder, a foam, a make-up, a stick, an aerosol, or embedded or absorbed in a wipe.

10. The method of claim 1, wherein the cosmetic composition is adapted for use as a body moisturizing oil, a body moisturizing lotion, a body moisturizing gel, a body moisturizing cream, a shaving preparation, a skin powder, a suntan lotion, an anti-acne preparation, a peeling preparation, a shampoo, a hair conditioners, a hair tonic, a hair styling cream, a hair styling gel, a pomade, a hair rinse, a hair-straightening preparation, a hair-setting preparation, a hairspray, a hair dying or bleaching preparation, or a makeup.

11. The method of claim 1, wherein the cosmetic composition further comprises one or more cosmetic adjuvants selected from the group consisting of additional fats or lipids, organic solvents, thickeners, binders, conditioning agents, demulcents, opacifiers, stabilizers, buffering agents, humectants, pigments, dyes, viscosity modifiers, emollients, antiperspirants, anti-foaming agents, foam boosters, hair colorants, hair perming agents, hair growth or restorer agents, hair loss prevention agents, abrasives, absorbents, anti-acne agents, anti-caking agents, moisturizing agents, perfumes or fragrances, preservatives, sunscreens, astringents, propellants, bleaching or lightening agents for skin or hair, tanning agents, deposition aids, suspending agents, polymers, fillers, sequestrants, bactericides, odor absorbers, antifungal agents, alkalinizing or acidifying agents, pearlescent aids, chelants, proteins, anti-dandruff agents, surfactants, emulsifiers, anti-free radical agents, antioxidants, vitamins, and α-hydroxy acids.

12. The method of claim 1, wherein the cosmetically acceptable carrier comprises water and the cosmetic composition is in the form of a lotion or cream emulsion with an aqueous phase and an oily phase comprising a tobacco seed oil, the cosmetic composition further comprising one or more cosmetic adjuvants selected from the group consisting of additional oils, thickeners, surfactants, preservatives, pigments, humectants, emollients, occlusives, and combinations thereof.

13. The method of claim 1, wherein the cosmetic composition further comprises one or more emollients in an amount of about 0.01 to about 20% by weight of the cosmetic composition.

14. The method of claim 1, wherein the cosmetic composition further comprises one or more humectants in an amount of about 0.01 to about 10% by weight of the cosmetic composition.

15. The method of claim 1, wherein the cosmetic composition further comprises one or more surfactants in an amount of about 0.01 to about 50% by weight of the cosmetic composition.

16. The method of claim 1, wherein the cosmetic composition further comprises one or more conditioning agents in an amount of about 0.01 to about 5% by weight of the cosmetic composition.

17. The method of claim 1, wherein the cosmetic composition further comprises one or more preservatives in an amount of about 0.01 to about 10% by weight of the cosmetic composition.

18. The method of claim 1, wherein the cosmetic composition further comprises one or more thickening agents in an amount of about 0.01 to about 15% by weight of the cosmetic composition.

19. The method of claim 1, wherein the cosmetic composition further comprises one or more emulsifiers in an amount of about 0.01 to about 15% by weight of the cosmetic composition.

20. The method of claim 1, wherein the cosmetic composition further comprises one or more antioxidants in an amount of about 0.01 to about 10% by weight of the cosmetic composition.

21. The method of claim 1, wherein the cosmetic composition further comprises one or more natural or essential oils in an amount of about 0.01 to about 20% by weight of the cosmetic composition.

22. The method of claim 1, wherein the cosmetic composition further comprises one or more occlusives in an amount of about 0.01 to about 5% by weight of the cosmetic composition.

23. The method of claim 1, wherein the cosmetic composition further comprises one or more agents useful for treating wrinkles in the skin in an amount of about 0.01 to about 5% by weight of the cosmetic composition.

24. The method of claim 1, wherein the cosmetic composition is in the form of an emulsion adapted for moisturizing skin, the cosmetic composition comprising water in an amount up to about 80% by weight, the refined tobacco seed oil in an amount up to about 10% by weight, one or more emollients in an amount up to about 20% by weight, one or more emulsifiers in an amount up to about 15% by weight, and one or more humectants in an amount up to about 10% by weight.

25. The method of claim 1, wherein the cosmetic composition is in the form of an emulsion adapted for cleansing skin or hair, the cosmetic composition comprising water in an amount up to about 80% by weight, the refined tobacco seed oil in an amount up to about 10% by weight, one or more emulsifiers in an amount up to about 15% by weight, and one or more surfactants in an amount up to about 50% by weight.

* * * * *